(12) United States Patent
Hirose et al.

(10) Patent No.: US 8,740,994 B2
(45) Date of Patent: Jun. 3, 2014

(54) DYEING AGENT AND USE FOR SAME

(75) Inventors: Yoshihiko Hirose, Kakamigahara (JP); Yukihide Sato, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 0 days.

(21) Appl. No.: 14/116,757

(22) PCT Filed: May 10, 2012

(86) PCT No.: PCT/JP2012/061937
§ 371 (c)(1),
(2), (4) Date: Nov. 8, 2013

(87) PCT Pub. No.: WO2012/153791
PCT Pub. Date: Nov. 15, 2012

(65) Prior Publication Data
US 2014/0068875 A1   Mar. 13, 2014

(30) Foreign Application Priority Data

May 11, 2011 (JP) ................................. 2011-106532
Jul. 12, 2011 (JP) ................................. 2011-154209
Dec. 1, 2011 (JP) ................................. 2011-263158

(51) Int. Cl.
*A61Q 5/10* (2006.01)
*A61K 8/66* (2006.01)

(52) U.S. Cl.
CPC .... *A61Q 5/10* (2013.01); *A61K 8/66* (2013.01)
USPC .................................................. 8/405; 8/401

(58) Field of Classification Search
CPC .... A61Q 5/10; A61K 8/66; A61K 2800/4324
USPC .................................................... 8/405, 401
See application file for complete search history.

(56) References Cited

U.S. PATENT DOCUMENTS

| 6,152,967 A | 11/2000 | Maubru |
| 6,730,133 B1 | 5/2004 | Plos et al. |
| 7,288,120 B2 * | 10/2007 | Pereira et al. ..................... 8/405 |
| 2004/0064901 A1 | 4/2004 | Kleen et al. |
| 2006/0021156 A1 | 2/2006 | Lang et al. |

FOREIGN PATENT DOCUMENTS

| JP | 09503130 A | 3/1997 |
| JP | 2000502412 A | 2/2000 |
| JP | 2000502757 A | 3/2000 |
| JP | 2000516264 A | 12/2000 |
| JP | 2001139441 A | 5/2001 |
| JP | 2004522709 A | 7/2004 |
| JP | 2005290013 A | 10/2005 |
| WO | WO-9509909 A1 | 4/1995 |
| WO | WO-9723684 A1 | 7/1997 |
| WO | WO-9723685 A1 | 7/1997 |

* cited by examiner

*Primary Examiner* — Eisa Elhilo
(74) *Attorney, Agent, or Firm* — Edwards Wildman Palmer LLP; James E. Armstrong, IV; Edmund J. Koundakjian

(57) ABSTRACT

The object is to provide a process for dyeing that can provide an excellent dyeing effect while utilizing an oxidase, and a dyeing agent for use in the process. Provided is a dyeing agent comprising a modified enzyme obtained by adding positive charge by a chemical modification with an amine to an enzyme selected from the group consisting of an enzyme specified as EC 1.10.3.1, an enzyme specified as EC 1.10.3.2, an enzyme specified as EC 1.3.3.5, an enzyme specified as EC 1.10.3.4, an enzyme specified as EC 1.10.3.3 and an enzyme specified as EC 1.14.18.1. A process for dyeing using the dyeing agent is also provided.

13 Claims, 20 Drawing Sheets

DYEING AGENT AND USE FOR SAME

TECHNICAL FIELD

The present invention relates to a dyeing agent and use thereof. Specifically, the present invention relates to a dyeing agent and a process for dyeing using a modified oxidase. The present application claims priority based on Japanese Patent Application No. 2011-106532 filed on May 11, 2011, priority based on Japanese Patent Application No. 2011-154209 filed on Jul. 12, 2011 and priority based on Japanese Patent Application No. 2011-263158 filed on Dec. 1, 2011, and all of the contents of these patent applications are incorporated by reference.

BACKGROUND ART

Dyeing processes utilizing oxidation dye such as phenylenediamines and aminophenols are frequently used in dyeing of keratin fibers, specifically human hairs and the like, by utilizing the advantages that dyeing in various color tones is possible and the duration is long, as well as that the dyeing time is short, and the like. Hydrogen peroxide has been conventionally used for the color development of oxidation dyes. However, hydrogen peroxide has a strong irritant property, and hairs and scalps and the like are damaged by using hydrogen peroxide. In order to overcome such problem, use of an oxidase instead of hydrogen peroxide has been attempted (for example, see Patent Documents 1 to 3).

PRIOR ART DOCUMENT

Patent Documents

Patent Document 1: Japanese Patent No. 3943133
Patent Document 2: Japanese Translation of PCT International application Publication No. 2000-502757
Patent Document 3: Japanese Unexamined Patent Application Publication No. 2001-139441

SUMMARY OF THE INVENTION

Problems to be Solved by the Invention

A sufficient dyeing effect was obtained in the dyeing processes using oxidases that had been reported in the past, and thus the processes were far from practical use. Therefore, the object of the present invention is to provide a process for dyeing that can provide an excellent dyeing effect when utilizing an oxidase, and a dyeing agent for use in the process.

Means for Solving the Problem

The present inventors researched by using bilirubin oxidase, which is one of oxidases, under the conception that the affinity of an enzyme for a material is especially important in a process for dyeing using an oxidase. The inventors did many studies aiming at improving the dyeing effect, for example, in the dyeing of human hairs, and consequently showed that the dyeing effect is dramatically increased by using bilirubin oxidase to which positive charge has been added by a chemical modification with an amine (referred to as modified BO or PMO). Furthermore, they also observed a fine dyeing property also at a relatively low pH. Furthermore, it was clarified that dyeing by modified BO is excellent in shampoo resistance. Accordingly, it was clarified by the studies of the present inventors that a modification by adding positive charge by a chemical modification with an amine is effective for exerting a high dyeing effect. In addition, in the dyeing using a modified enzyme, a specific color tone that is different from that in the case when an unmodified enzyme is used was obtained. This fact is an important and meaningful finding in applying a dyeing process and a dyeing agent using a modified enzyme.

It was clarified as a result of further studies that a modified enzyme enhances the dyeing effect also in the case when an indole compound, which is considered to be safer, is used as a chromogenic substrate. Furthermore, the dyeing by the modified enzyme was excellent in shampoo resistance. Furthermore, it was confirmed that a color (color tone) in dyeing can be adjusted by using two or more kinds of indole compounds in combination.

The inventions shown below are based on the above-mentioned achievements and findings.

[1] A dyeing agent comprising a modified enzyme obtained by adding positive charge by a chemical modification with an amine to an enzyme selected from the group consisting of an enzyme specified as EC 1.10.3.1, an enzyme specified as EC 1.10.3.2, an enzyme specified as EC 1.3.3.5, an enzyme specified as EC 1.10.3.4, an enzyme specified as EC 1.10.3.3 and an enzyme specified as EC 1.14.18.1.

[2] The dyeing agent according to [1], which is formed by combining with an oxidation dye.

[3] The dyeing agent according to [2], which is a one-component type containing the oxidation dye and the modified enzyme.

[4] The dyeing agent according to [2], which is a two-component type consisting of a first element containing the oxidation dye and a second element containing the modified enzyme.

[5] The dyeing agent according to any one of [1] to [4], which is for use in dyeing keratin fibers.

[6] The dyeing agent according to [5], wherein the keratin fibers are human hairs.

[7] The dyeing agent according to any one of [2] to [6], wherein the oxidation dye is one or more compound(s) selected from the group consisting of phenylenediamine, aminophenol, cresol, toluenediamine, naphthol, indole, indoline and derivatives thereof.

[8] The dyeing agent according to any one of claims [2] to [6], wherein the oxidation dye is one or more compound(s) selected from the group consisting of paraphenylenediamine, paraminophenol, paratoluenediamine, 4-aminoindole, 5-aminoindole, 6-aminoindole, 4-hydroxyindole and 5,6-dihydroxyindole.

[9] The dyeing agent according to any one of [1] to [8], wherein the enzyme is bilirubin oxidase.

[10] A process for dyeing, comprising a step of treating fibers or processed fibers with the dyeing agent according to any one of [1] to [9].

[11] The process for dyeing according to [10], wherein the fibers are keratin fibers.

[12] The process for dyeing according to [11], wherein the keratin fibers are human hairs.

[13] The process for dyeing according to [12], wherein the treatment is conducted under a condition of a pH of 7.0 to 8.0.

DESCRIPTION OF EMBODIMENTS

1. Dyeing Agent

Figure 1:
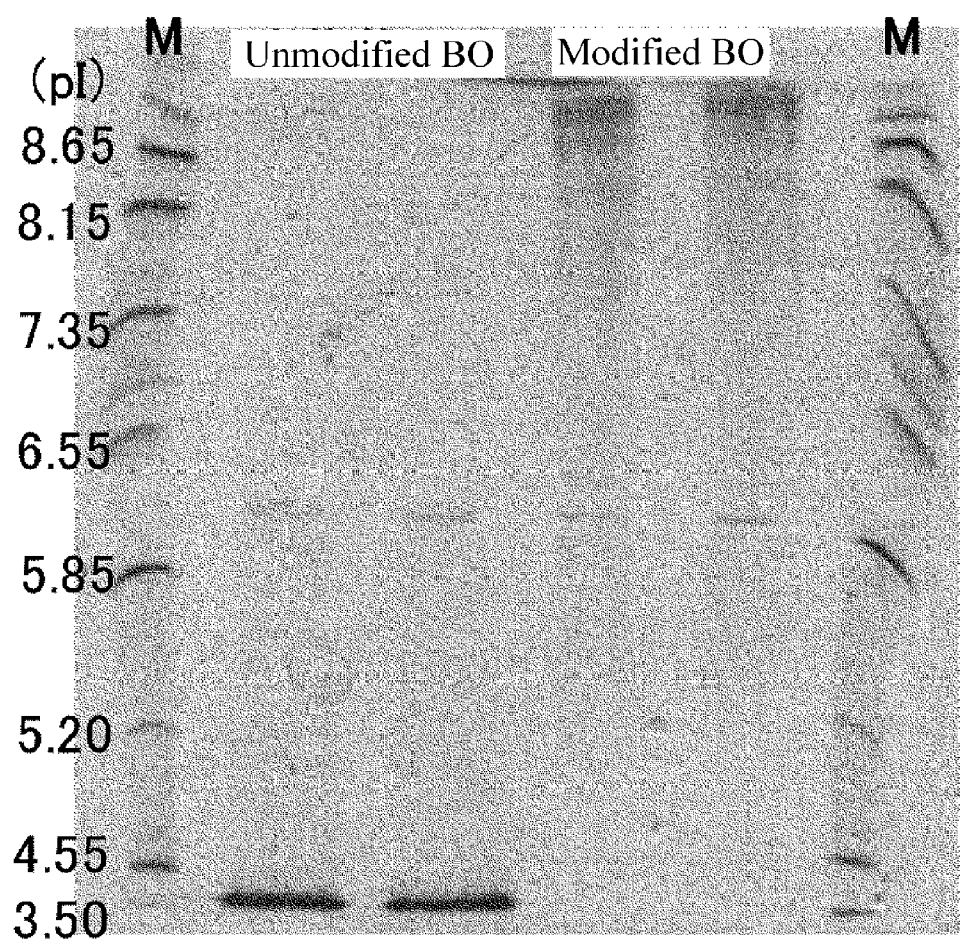
FIG. 1 is the result of the isoelectric focusing for the modified BO. M is a molecular weight marker.

The first aspect of the present invention relates to a dyeing agent used for dyeing fibers or processed fibers. The dyeing agent of the present invention is used for the dyeing of, for example, fibers, yarns, fabrics, woven fabrics or clothes or the like formed of keratin, cotton, diacetate, flax, linen, lyocell, polyacrylics, polyamides, polyesters, ramie, rayon, Tencel (registered trademark) or triacetate. The dyeing agent of the present invention contains an oxidase that has undergone a predetermined modification (hereinafter referred to as "modified enzyme"). The dyeing agent of the present invention acts on an oxidation dye to exert a desired dyeing effect. Therefore, the dyeing agent of the present invention is typically used in combination with an oxidation dye. In the present description, the expression "used in combination" or "formed by combining with" refers to that the oxidation dye and the modified enzyme are used in combination. In an exemplary embodiment, the dyeing agent of the present invention is provided as a composition in which the oxidation dye and the modified enzyme are mixed. The dyeing agent of the embodiment is referred to as a one-component type dyeing agent. On the other hand, it is also possible to provide the dyeing agent of the present invention in the form of a kit comprising a first element containing the oxidation dye and a second element containing the modified enzyme. The dyeing agent of the embodiment is referred to as a two-component type dyeing agent. In the case of the two-component type dyeing agent, the respective elements are provided in the state that they are housed in separated containers or compartments, and the two elements are mixed upon use. Meanwhile, it can be considered that the one-component type dyeing agent is superior to the two-component type dyeing agent in that it has a simple constitution and can attain an easier process of use.

(1) Dye

In the present description, the term "oxidation dye" refers to a dye that requires an oxidation reaction for color development or dyeing. The oxidation dye includes "a dye precursor" that develops a color by the oxidative polymerization of the precursor itself, and "a dye aid (coupler)" that exhibits an inherent color tone by being polymerized with a dye precursor. A suitable oxidation dye is adopted depending on the intended use of the dyeing agent of the present invention. Examples of the oxidation dye include acridine, anthracene, azulene, benbene, benzofuran, benzothiazole, benzothiazoline, carboline, carbazole, cinnoline, chromane, chromene, chrysene, fulvene, furan, imidazole, indazole, indene, indole, indoline, indolizine, isothiazole, isoquinoline, isoxazole, naphthalene, naphthylene, naphthylpyridine, oxazole, perylene, phenanthrene, phenazine, phthalazine, pteridin, purine, pyran, pyrazole, pyrene, pyridazine, pyridazone, pyridine, pyrimidine, pyrrole, quinazoline, quinoline, quinoxaline, sulfonyl, thiophene, triazine, or derivatives or substituted forms thereof, 3,4-diethoxyaniline, 2-methoxy-p-phenylenediamine, 1-amino-4-b-methoxyethylaminobenzene(N-b-methoxyethyl-p-phenylenediamine), 1-amino-4-bis-(b-hydroxyethyl)-aminobenzene (N,N-bis-(b-hydroxyethyl)-p-phenylenediamine, 2-methyl-1,3-diaminobenzene (2,6-diaminotoluene), 2,4-diaminotoluene, 2,6-diaminotoluene, 1-amino-4-sulfonato-benzene, 1-N-methylsulfonato-4-aminobenzene, 1-methyl-2-hydroxy-4-aminobenzene (3-amino-o-cresol), 1-methyl-2-hydroxy-4-b-hydroxyethylaminobenzene (2-hydroxy-4-b-hydroxyethylamino-toluene), 1-hydroxy-4-methylaminobenzene (p-methylaminophenol), 1-methoxy-2,4-diaminobenzene 2,4-diaminoanisole), 1-ethoxy-2,3-diaminobenzene (2,4-diaminophenethol), 1-b-hydroxyethyloxy-2,4-diamino-benzene (2,4-diaminophenoxyethanol), 1,3-dihydroxy-2-methylbenzene (2-methylresorcinol), 1,2,4-trihydroxybenzene, 1,2,4-trihydroxy-5-methylbenzene (2,4,5-trihydroxytoluene), 2,3,5-trihydroxytoluene, 4,8-disulfonato-1-naphthol, 3-sulfonato-6-amino-1-naphthol (J-acid), 6,8-disulfonato-2-naphthol, 1,4-phenylenediamine, 2,5-diaminotoluene, 2-chloro-1,4-phenylenediamine, 2-aminophenol, 3-aminophenol, 4-aminophenol, 1,3-phenylenediamine, 1-naphthol, 2-naphthol, 4-chlororesorcinol, 1,2,3-benzenetriol (pyrogallol), 1,3-benzenediol (resorcinol), 1,2-benzenediol (pyrocatechol), 2-hydroxy-cinnamic acid, 3-hydroxy-cinnamic acid, 4-hydroxy-cinnamic acid, 2,3-diaminobenzoic acid, 2,4-diaminobenzoic acid, 3,4-diaminobenzoic acid, 3,5-diaminobenzoic acid, methyl 2,3-diaminobenzoate, ethyl 2,3-diaminobenzoate, isopropyl 2,3-diaminobenzoate, methyl 2,4-diaminobenzoate, ethyl 2,4-diaminobenzoate, isopropyl 2,4-diaminobenzoate, methyl 3,4-diaminobenzoate, ethyl 3,4-diaminobenzoate, isopropyl 3,4-diaminobenzoate, methyl 3,5-diaminobenzoate, ethyl 3,5-diaminobenzoate, isopropyl 3,5-diaminobenzoate, N,N-dimethyl-3,4-diaminobenzoic acid amide, N,N-diethyl-3,4-diaminobenzoic acid amide, N,N-dipropyl-3,4-diaminobenzoic acid amide, N,N-dibutyl-3,4-diaminobenzoic acid amide, 4-chloro-1-naphthol, N-phenyl-p-phenylenediamine, 3,4-dihydroxybenzaldehyde, pyrrole, pyrrole-2-isonomidazole, 1,2,3-triazole, benzotriazole, benzimidazole, imidazole, indole, 1-amino-8-hydroxynaphthalene-4-sulfonic acid (S-acid), 4,5-dihydroxynaphthalene-2,7-disulfonic acid (chromotropic acid), anthranilic acid, 4-aminobenzoic acid (PABA), 2-amino-8-naphthol-6-sulfonic acid (gamma acid), 5-amino-1-naphthol-3-sulfonic acid (M-acid), 2-naphthol-3,6-disulfonic acid (R-acid), 1-amino-8-naphthol-2,4-disulfonic acid (Chicago acid), 1-naphthol-4-sulfonic acid (Nevile-Winther acid), peri acid, N-benzoyl J-acid, N-phenyl J-acid, 1,7-krebes acid, 1,6-krebes acid, Bon acid, Naphthol AS Disperse Black 9, Naphthol AS OL, Naphthol AS PH, Naphthol AS KB, Naphthol AS BS, Naphthol AS D, Naphthol AS B1, Mordant Black 3CI 14640 (Eriochrome Blue Black B), 4-amino-5-hydroxy-2,6-naphthalenedisulfonic acid (H-acid), Fat Brown RR Solvent Brown 1 (CI 11285), hydroquinone, mandelic acid, melamine, o-nitrobenzaldehyde, 1,5-dihydroxynaphthalene, 2,6-dihydroxynaphthalene, 2,3-dihydroxynaphthalene, benzylimidazole, 2,3-diaminonaphthalene, 1,5-diaminonaphthalene, 1,8-diaminonaphthalene, salicylic acid, 3-aminosalicylic acid, 4-amino salicylic acid, 5-aminosalicylic acid, methyl-3-aminosalicylate, methyl-4-aminosalicylate, methyl-5-aminosalicylate, ethyl-3-aminosalicylate, ethyl-4-aminosalicylate, ethyl-5-aminosalicylate, propyl-3-aminosalicylate, propyl-4-amino salicylate, propyl-5-aminosalicylate, salicylic acid amide, 4-aminothiophenol, 4-hydroxythiophenol, aniline, 4,4'-diaminodiphenylaminesulfate, 4-phenylazoaniline, 4-nitroaniline, N,N-dimethyl-1,4-phenylenediamine, N,N-diethyl-1,4-phenylenediamine, Disperse Orange 3, Disperse Yellow 9, Disperse Blue 1, N-phenyl-1,2-phenylenediamine, 6-amino-2-naphthol, 3-amino-2-naphthol, 5-amino-1-naphthol, 1,2-phenylenediamine, 2-aminopyrimidine, 4-aminoquinaldine, 2-nitroaniline, 3-nitroaniline, 2-chloroaniline, 3-chloroaniline, 4-chloroaniline, 4-(phenylazo)resorcinol (Sudan Orange G, CI 11920), Sudan Red B, CI-26110, Sudan Red B, CI-26050, 4'-aminoacetanilide, alizarin, 1-anthramine (1-aminoanthracene), 1-aminoanthraquinone, anthraquinone, 2,6-dihydroxyanthraquinone (anthraflavic acid), 1,5-dihydroxyanthraquinone (anthrarufin), 3-aminopyridine (nicotinamide), pyridine-3-carboxylic acid (nicotinic acid), Mordant Yellow 1, Alizarin Yellow GG, GI 14025, Coomassie Blue Gray, Acid Black 48, CI-65005, Palantine Fast Black WAN, And Black 52, CI-15711, Palantine Chrome Black 6BN, CI 15705, Eriochrome Blue Black R Mordant Black 11, Eriochrome Black T, Naphthol Blue Black, Acid Black 1, CI-20470, 1,4-dihydroxyanthraquinone (quinizarin), 4-hydroxycoumarin, umbelliferone, 7-hydroxycoumarin, esculetin 6,7-dihydroxycoumarin, coumarin, Chromotrope 2B Acid Red 176, CI 1657, Chromotrope 2B Acid Red 29, CI 16570, Chromotrope FB Acid Red 14, CI 14720, 2,6-dihydroxyisonicotinic acid, citrazinic acid, 2,5-dichloroaniline, 2-amino-4-chlorotoluene, 2-nitro-4-chloroaniline, 2-methoxy-4-nitroaniline, p-bromophenol. Aromatic compounds selected from phenylenediamine, aminophenol, cresol, phenol, naphthol, indole or indoline, or derivatives thereof are preferable. The derivatives used herein are those substituted by one or plural functional group(s) or substituent(s). The functional group(s) or substituent(s) that may be introduced herein are selected from the group consisting of halogens; sulfo; sulfonato; sulfamino; sulfanyl; amino; amide; nitro; azo; imino; carboxy; cyano; formyl; hydroxy; halocarbonyl; carbamoyl; carbamidoyl; phosphonato; phosphonyl; C1-18 alkyls; C1-18 alkenyls; C1-18 alkynyls; C1-18 alkoxys; C1-18 oxycarbonyls; C1-18 oxoalkyls; C1-18 alkylsulfanyls; C1-18 alkylsulfonyls; C1-18 alkyliminos or amino, and the respective C1-18 alkyls, C1-18 alkenyls and C1-18 alkynyl groups may be mono-, di- or poly-substituted by any of the above-mentioned functional group(s) or substituent(s).

The dyeing agent of the present invention is specifically useful for the dyeing of keratin fibers (human hairs, hairs of cows, horses, sheep, goats, alpacas, Angora rabbits and the like, etc.). Examples of the oxidation dye that is preferable for constituting the dyeing agent of the present invention for dyeing keratin fibers include paraphenylenediamines, metaphenylenediamines, orthophenylenediamines, paraminophenols, metaminophenols, orthoaminophenols, pyridine derivatives, pyrimidine derivatives, pyrazole derivatives, metadiphenols, naphthols, indoline derivatives, indole derivatives and acid addition salts thereof (as the acid addition salts, for example, hydrochlorides, hydrobromides, sulfates, tartrates, lactates or acetates, and the like may be used.), indoline compounds, and indole compounds. Specific examples of these oxidation dyes are paraphenylenediamine, 5-aminoorthocresol, orthoaminophenol, metaminophenol, paraminophenol, 2,6-diaminopyridine, 5-(2-hydroxyethylamino)-2-toluenediamine, N,N-bis(β-hydroxy)-paraphenylenediamine sulfate, paranitro-orthophenylenediamine, paranitro-2',4'-diaminoazobenzene sodium sulfate, toluene-2,5-diamine, 5-aminoorthocresol sulfate, paraminophenol sulfate, orthochloro-paraphenylenediamine sulfate, 4,4'-diaminodiphenylamine sulfate, paramethylaminophenol sulfate, paraphenylenediamine sulfate, metaphenylenediamine sulfate, toluene-2,5-diamine sulfate, 2,4-diaminophenoxyethanol hydrochloride, toluene-2,5-diamine hydrochloride, metaphenylenediamine hydrochloride, 2,4-diaminophenol hydrochloride, 3,3'-iminodiphenol, paraphenylenediamine hydrochloride, N-phenyl-paraphenylenediamine hydrochloride, N-phenyl-paraphenylenediamine acetate, 1,5-dihydroxynaphthalene, tolylene-3,4-diamine, paramethylaminophenol, N,N-bis(4-aminophenyl)-2,5-diamino-1,4-quinonediimine, orthoaminophenol sulfate, 2,4-diaminophenol sulfate, metaminophenol sulfate, paratoluenediamine, indoline, 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 4-methoxy-6-hydroxyindoline, N-hexyl-5,6-dihydroxyindoline, 2-methyl-5,6-dihydroxyindoline, 3-methyl-5,6-dihydroxyindoline, 4-hydroxyindoline, 2,3-dimethyl-5,6-dihydroxyindoline, 2-methyl-5-ethyl-6-hydroxyindoline, 2-methyl-5-hydroxy-6-β-hydroxyethylindoline, 4-hydroxypropylindoline, 2-hydroxy-3-methoxyindoline, 6-hydroxy-5-methoxyindoline, 6-hydroxyindoline, 5-hydroxyindoline, 7-hydroxyindoline, 7-aminoindoline, 5-aminoindoline, 4-aminoindoline, 5,6-dihydroxyindoline carboxylic acid, 1-methyl-5,6-dihydroxyindoline, 4,5-dihydroxyindole, 5,6-dihydroxyindole, 6,7-dihydroxyindole, N-methyl-5,6-dihydroxyindole, N-ethyl-5,6-dihydroxyindole, N-hexyl-5,6-dihydroxyindole, 2-methyl-5,6-dihydroxyindole, 3-methyl-5,6-dihydroxyindole, 4-hydroxyindole, 2,3-dimethyl-5,6-dihydroxyindole, 2-methyl-5-ethyl-6-hydroxyindole, 2-methyl-5-hydroxy-6-β-hydroxyethylindole, 4-hydroxypropylindole, 2-hydroxy-3-methoxyindole, 4-hydroxy-5-methoxyindole, 6-hydroxy-7-methoxyindole, 6-hydroxy-5-methoxyindole, 6-hydroxyindole, 5-hydroxyindole, 7-hydroxyindole, 7-aminoindole, 6-aminoindole, 5-aminoindole, 4-aminoindole, 5,6-dihydroxyindole carboxylic acid, and 1-methyl-5,6-dihydroxyindole.

One or two or more kinds of oxidation dye(s) is/are used for the dyeing agent of the present invention. Combination use of two or more kinds of oxidation dyes is effective for improving the dyeing effect, adjusting the color (color tone), and the like. Specifically, in the case of constitution for dyeing keratin fibers, it is preferable to use a combination of an oxidation dye that is classified as a dye precursor (paraphenylenediamine, orthoaminophenol, paraminophenol, paratoluenediamine, 4-aminoindole, 5-aminoindole, 6-aminoindole, 4-hydroxyindole, 5,6-dihydroxyindole and the like) and an oxidation dye that is classified as a dye aid (metaphenylenediamine, metaminophenol, metadiphenol, naphthol, indole, indoline, indazole and the like).

The contained amount of the oxidation dye is not specifically limited, and the incorporation amount may be determined with consideration for the characteristic of the oxidation dye used, the intended use, and the like. In the case of the one-component type dyeing agent, the oxidation dye can be incorporated so as to be, for example, 0.01 to 20% by weight, preferably 0.05 to 10% by weight, further preferably 0.01 to 1% by weight, with respect to the whole amount of the dyeing agent. In the case of a two-component type dyeing agent, the oxidation dye can be incorporated so as to be, for example, 0.01 to 20% by weight, preferably 0.05 to 10% by weight, further preferably 0.01 to 1% by weight, with respect to the whole amount of the first element in which the oxidation dye is to be contained.

As a component that contributes to dyeing, a direct dye may be incorporated in addition to the oxidation dye. By incorporating the direct dye, the dyeing effect can be enhanced and the color tone of the dyeing can be adjusted. Examples of the direct dye include 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, picramic acid, sodium picramate, 2-amino-5-nitrophenol sulfate, resorcinol, nitro-p-phenylenediamine sulfate, p-nitro-o-phenylenediamine sulfate, p-nitro-m-phenylenediamine sulfate, Natural Orange 6 (2-hydroxy-1,4-naphthoquinone), Acid Orange 8, Acid Violet 17, Remazol Brilliant Blue, Evans Blue and Acid Blue 80.

The contained amount of the direct dye is also not specifically limited. In the case of a one-component type dyeing agent, the direct dye can be incorporated so as to be, for example, 0.01 to 20% by weight with respect to the whole amount of the dyeing agent. In the case of a two-component type dyeing agent, the direct dye is incorporated in the first element in which the oxidation dye is to be contained and/or the second element in which the modified enzyme is to be contained. The contained amount in this case is, for example, 0.01 to 20% by weight with respect to the whole amount of the first element, and for example, 0.01 to 20% by weight with respect to the whole amount of the second element. In addition, two or more kinds of direct dyes can be used in combination as is the case with the oxidation dyes.

(2) Modified Enzyme

In the present invention, an oxidase in which the positive charge possessed by the enzyme has been increased more as compared to a natural state (native) is used. In other words, an oxidase that has been modified so that positive charge is added is used. As the oxidase, catechol oxidase (EC 1.10.3.1), laccase (EC 1.10.3.2), bilirubin oxidase (EC1.3.3.5), o-aminophenol oxidase (EC 1.10.3.4), ascorbic acid oxidase (EC 1.10.3.3) or monophenol oxidase (EC 1.14.18.1) is used. Enzymes derived from plants (for example, derived from *Anacardiacea*, derived from *Magnifera* indica, derived from *Schinusmolle*, derived from *Pleiogynium timoriense*, derived from *Podocarpacea*), enzymes derived from animals, or enzymes derived from bacteria or fungi (for example, derived from *Aspergillus*, derived from *Botrytis*, derived from *Collybia*, derived from *Fomes*, derived from *Lentinus*, derived from *Myceliophthora*, derived from *Neurospora*, derived from *Pleurotus*, derived from *Podospora*, derived from *Scytalidium*, derived from *Trametes*, derived from *Rhizoctonia*, derived from *H. thermoidea*, and derived from *H. brevispora*) can be used. Alternatively, an enzyme produced by a gene recombination technique (recombinant enzyme) may be used.

In a preferable embodiment of the present invention, bilirubin oxidase is adopted as the oxidase. As the bilirubin oxidase, for example, those derived from microorganisms belonging to *Myrothecium, Coprinus, Penicillium* and *Bacillus* can be used. Examples of *Myrothecium* bacteria may include stock strains of *Myrothecium verrucaria* MT-1, FERM-BP 653 (see Agricultural and Biological Chemistry Vol. 45, pp. 2383-2384 (1981)), *Myrothecium verrucaria* IFO 6113, *Myrothecium verrucaria* IFO 6133, *Myrothecium verrucaria* IFO 6351, *Myrothecium verrucaria* IFO 9056, *Myrothecium cinctum* IFO 9950, *Myrothecium roridum* IFO 9531 and the like. Examples of *Coprinus* bacteria may include stock strains of *Coprinus cinereus* IFO 8371, *Coprinus lagopides* IFO 30120 and the like. Examples of *Penicillium* bacteria may include *Penicillium janthinellum* (See Japanese Unexamined Patent Application Publication No. 63-309187) and the like. Examples of *Bacillus* bacteria may include *Bacillus licheniformis* (see Japanese Unexamined Patent Application Publication No. 61-209587). A purified preparation of an enzyme bilirubin oxidase can be obtained by liquid-culturing or solid-culturing these strains by a conventional method, and conducting extraction, salting-out, dialysis, ion exchange, gel permeation or the like from the culture liquid. On the other hand, bilirubin oxidases derived from *Schizophyllum commune* (See Japanese Unexamined Patent Application Publication No. 59-135886), derived from Asteraceae plants (see Japanese Unexamined Patent Application Publication No. 62-285782) and derived from alfalfa (see Japanese Unexamined Patent Application Publication No. 6-319536), or recombinants (see Japanese Unexamined Patent Application Publication No. 5-199882) are also known, and these bilirubin oxidases can also be used. Furthermore, bilirubin oxidases are also commercially available (from Amano Enzyme Inc., Takara Bio Inc., Asahi Kasei Corporation, Sigma-Aldrich Corporation and the like), and such commercial products may also be used.

Positive charge has been added to the enzyme used in the present invention by a chemical modification using an amine (a diamine or a polyamine (a triamine, a tetraamine or the like) (hereinafter an enzyme that has undergone such modification is referred to as "modified enzyme"). In other words, the positive charge has been increased by the addition of an amino group. The means for such modification itself is well-known, and for example Methods for Chemical Modification of Proteins, <Vol. 1> and <Vol. 2> (Gakkai Shuppan Center, Ohno et al.) Protein Hybrids (Kyoritsu Shuppan, edited by Inada) and the like may be referred to. Examples of the amines that can be utilized in the chemical modification include n-butylamine, ethylenedimine, putrescine, 3,3'-diaminodipropylamine, agmatine, N,N-bis(3-aminopropyl)-1,4-butanediamine, bis(hexamethylene)triamine, 1,5-diaminopentane, diethylenetriamine, spermine, sperdine, or salts thereof, and the like.

It is also possible to add positive charge by substituting a part of the amino acid residues constituting the enzyme with other amino acid residue(s). Specifically, acidic amino acid residue(s) (for example, aspartic acid, glutamic acid) among the constitutional amino acid residues may be substituted by neutral amino acid(s) (for example, glutamine, asparagine, serine) or basic amino acid(s) (for example, arginine, histidine, lysine) by using a gene-engineered means. For such substitution of amino acid residue(s), a site-directed mutagenesis process (Molecular Cloning, Third Edition, Chapter 13, Cold Spring Harbor Laboratory Press, New York) or a random mutagenesis process (Molecular Cloning, Third Edition, Chapter 13, Cold Spring Harbor Laboratory Press, New York) can be used.

In order to increase the addition amount of positive charge, the substitution of the amino residue(s) as mentioned above is preferably conducted on two or more amino acid residues. However, if the number of the substituted amino acid residues is too much, the enzymatic activity may be affected; therefore, it is preferable to substitute, for example, about 2 to 10 amino acid residues, depending on the enzyme to be modified.

The amino acid residues to be substituted may be selected and specified based on whether the enzymatic activity is affected or not as an indication. Namely, it is preferable to conduct substitution after specifying the amino acid residues that do not affect the enzymatic activity (or are unlikely to affect) by utilizing a result of a steric structure analysis and the like. On the other hand, it is preferable to target the amino acid residues positioned on the surface in the steric structure for the substitution. When specific examples of the modification by substitution of amino acid residue(s) are shown, in the case of bilirubin oxidase consisting of the amino acid sequence of SEQ ID NO: 1, preferable candidates for the substitution are 91st Asp, 96th Asp, 126th Glu, 151st Glu, 181st Glu, 233rd Glu, 280th Asp, 323rd Asp, 366th Asp, 376th Asp, 408th Asp, 516th Asp, 529th Glu, and 538th Glu. Therefore, it is preferable to substitute one or two or more of these with basic amino acid(s).

Whether the intended modification has been achieved or not may be judged by, for example, comparing isoelectric points (pI) between the enzyme after the modification and the enzyme before the modification (typically a native enzyme). Namely, if the enzyme after the modification has a higher isoelectric point than that of the enzyme before the modification as a result of the comparison of the isoelectric points by isoelectric focusing or the like, it can be judged that the desired modification (addition of positive charge) has been conducted. On the other hand, in the case when amino groups are added, the presence or absence and degree, and the like of the modification can be judged by quantifying the amino groups.

An enzyme that has undergone other modification in addition to the above-mentioned modification may also be used. The "other modification" as used herein may include chemical modifications by water-soluble polymer substances (polyalkylene glycols, polyvinyl alcohols, polysaccharides, partially hydrolyzed or partially half-esterified copolymers of styrene and maleic anhydride, partially hydrolyzed or partially half-esterified copolymers of divinyl ether and maleic anhydride, partially hydrolyzed or partially half-esterified copolymers of acrylic acid and maleic anhydride, Ficoll, polyamino acids, albumin and the like) (Japanese Unexamined Patent Application Publication No. 64-60375), a modification by an acryloyl group (Japanese Unexamined Patent Application Publication No. 2009-044997), and the like. The purpose of the "other modification" is not specifically limited. For example, the "other modification" is conducted aiming at improving the stability, activity and/or storage stability, or modifying the substrate specificity, of the enzyme, and the like.

(3) Other Components

The dyeing agent of the present invention may contain additional components (optional components) besides the above-mentioned respective components. As the optional components, reducing agents such as alkaline compounds, picramic acid, sodium sulfite and N-acetyl-L-cysteine, surfactants, oil-based components, silicones, thickening agents, solvents, water, chelating agents, amino acids, various salts, moisturizing agents, antiseptic agents, UV inhibitors, alcohols, polyhydric alcohols, perfume materials and the like can be exemplified.

In the case when the dyeing agent of the present invention is constituted for dyeing of keratin fibers, it is preferable to incorporate an alkaline compound. According to the dyeing agent containing the alkaline compound, when the dyeing agent is applied, the swelling of the keratin fibers is promoted, and thus the dyeing effect is improved. The incorporation amount of the alkaline compound is preset so that a desired pH (for example, pH 7.0-10.0) can be attained upon use. An example of the incorporation amount of the one-component type dyeing agent is 0.01 to 20% by weight with respect to the whole amount of the dyeing agent. On the other hand, in the case of the two-component type dyeing agent, in principle, the alkaline compound is incorporated in the first element in which the oxidation dye is to be incorporated, and the incorporation amount is, for example, 0.01 to 20% by weight with respect to the whole amount of the first element (however, the alkaline compound may be incorporated in the second element instead of the first element, or the alkaline compound may be incorporated in both of the first element and second element). In addition, specific examples of the alkaline compound may include amine compounds such as monoethanolamine, monoisopropanolamine, triethanolamine and diethanolamine, inorganic compounds such as ammonia, sodium hydroxide, potassium hydroxide, ammonium carbonate, sodium carbonate, sodium hydrogen carbonate, potassium carbonate and potassium hydrogen carbonate, and the like.

The dyeing agent of the present invention is prepared into forms such as a paste (cream) form, an aerosol form, a gel form, a liquid form and a mousse form. In the case of a two-component type consisting of the first element (including the oxidation dye) and the second element (including the modified enzyme), the forms of the first element and second element are not necessarily the same.

2. Dyeing Process

The second aspect of the present invention relates to a dyeing process using the dyeing agent of the present invention. In the dyeing process of the present invention, fibers or processed fibers (they are collectively referred to as "material to be dyed") are treated with the dyeing agent of the present invention under a condition in which oxygen is present (namely, under an oxygen atmosphere). In the case of a one-component type dyeing agent, for example, the dyeing agent is diluted as necessary, and thereafter applied to a material to be dyed. Alternatively, the material to be dyed is immersed in a solution in which the dyeing agent is dissolved.

In the case of the two-component type dyeing agent, for example, the first element and second element are mixed (where necessary, they may be diluted or dissolved in a solvent), and thereafter applied to the material to be dyed. One element (the first element or second element) may be applied on the material to be dyed and then the other element may be applied on the material to be dyed so that the both elements are mixed on the surface and the like of the material to be dyed. Alternatively, the material to be dyed may be immersed in a solution in which the first element and second element are dissolved.

By the operations as mentioned above, a state in which the dyeing agent is contacting with the material to be dyed is formed. Furthermore, the contacting state is maintained for a time required for desired dyeing. At this time, it is also possible to retain the temperature or to warm for enhancing the dyeing effect or for rapid or efficient dyeing. In the case when the material to be dyed is human hairs, i.e., for example, in the case when the human hairs are dyed by the dyeing process of the present invention, the contacting state is maintained for about 10 minutes to 2 hours, preferably for about 20 minutes to 1 hour.

The pH condition during the treatment depends on the dyeing agent used. However, it is also possible to adjust the pH by separately using a pH adjusting agent. The pH during the treatment is, for example, pH 7.0-9.0. As shown in the following Examples, in the cases when modified bilirubin oxidases to which positive charge had been added were used, high dyeing effects were shown even under conditions of relatively low pHs. Based on this finding, in an exemplary embodiment of the present invention, the treatment is conducted under a condition of pH 7.0 to pH 8.0. By adopting the condition, damaging of a material to be dyed associated with dyeing can be decreased. The condition is specifically effective in dyeing human hairs, and it becomes possible to decrease the damage of the human hairs and the stimulation to the skin (scalp).

After the above-mentioned treatment, the material to be dyed is, in general, washed and finally dried. For example, water, a detergent or the like can be used for the washing. Furthermore, as the means for the drying, air drying (natural drying), hot air drying, spin drying, suction drying, barrel drying and the like can be exemplified.

In the dyeing process of the present invention, the oxidation and polymerization of the oxidation dye are caused by the action of the modified enzyme, thereby the material to be dyed is dyed. In the present invention, since an enzyme is utilized for the oxidation reaction, the damage of the material to be dyed associated with the dyeing treatment is little. Furthermore, the possibilities for adverse effects (allergic response) on the scalp and the like are decreased in the case when the dyeing process is applied to the hairs. On the other hand, the enzyme used in the present invention shows high affinity for the material to be dyed by the above-mentioned modification. By this characteristic, an enzymatic reaction (i.e., oxidation of the oxidation dye) effectively proceeds, and thus the dyeing effect is improved. Accordingly, the dyeing agent of the present invention enables effective dyeing while decreasing the influences on the material to be dyed and the like.

3. Other Use

The modified enzyme in the present invention is also effective as a component for permanent wave agents. In a treatment for making permanent waves, the disulfide bonds (S—S) in the hairs are cut by an agent 1 comprising a reducing agent (thioglycolic acid, thioglycolates, cystein, hydroxycystein, dihydroxycystein, acetylated cystein, sodium sulfite and the like) as a main component, and the hairs are then treated by an agent 2 comprising an oxidizing agent as a main component to thereby reform the cut S—S bonds. As the oxidizing agent, sodium bromate, perborate, hydrogen peroxide and the like are used. Instead of such oxidizing agents, the modified enzyme of the present invention can be used. In the case when the modified enzyme of the present invention is used, it is possible to constitute a one-component type permanent wave agent.

EXAMPLES

The following experiments were conducted aiming at improving the dyeing effect in a dyeing process using an oxidase. Specifically, bilirubin oxidase (BO), which is one of oxidation enzymes, was modified, and the influence on the dyeing effect was examined. Dyeing on human hairs was used as an index.

A. Modification of BO

1. Process (1) Modification with Amino Group

Modification to add an amino group was conducted on BO by the following process. 1,000 equivalent amount of putrescine, 100 equivalent amount of N-hydroxysuccinimide and 200 equivalent amount of water-soluble carbodiimide (EDC) on the basis of molar ratio were added to 200 mg of BO (derived from *Myrothecium verrucaria*, manufactured by Amano Enzyme Inc.), adjusted to 20 ml with 20 mM HEPES (pH 6.5), and reacted at 4° C. for 1 day. The pH of the putrescine was adjusted with diluted sulfuric acid.

(2) Purification of Sample

In order to remove the unreacted putrescine from the sample after the reaction, the sample was purified by a 10DG column (BIO-RAD) that had been equilibrated with a 20 mM borate buffer solution (pH 9.0).

(3) Measurement of Activity 30 mg of a reagent bilirubin was dissolved in 1.0 ml of a 0.05 mol/L phosphate buffer solution (pH 7.0) (containing 0.05 mmol/L EDTA) to give a substrate solution. Sodium cholate was dissolved so as to become 1% in a 0.05 mol/L phosphate buffer solution (pH 7.0) (containing 0.05 mmol/L EDTA), and 3 ml of this was mixed with 0.2 ml of the substrate solution and 0.1 ml of the enzyme solution and then reacted at 37° C., and a measurement was conducted based on the decrease in the absorbance at 460 nm. The amount of the enzyme required for oxidizing 1 μmol of bilirubin in 1 minute is defined as 1 unit.

(4) Isoelectric Focusing In order to compare the electrical charge with that of unmodified BO, isoelectric focusing was conducted.

(5) Quantification of Amino Group

The amino group was quantified by the following process. The protein amounts in measurement samples were unified (within the range of protein amount: 0.6-1.0 mg/ml), and then the prepared sample (0.25 ml), 4% NaHCO$_3$ (0.25 ml) and an aqueous solution of 0.1% TNBS (0.25 ml) were mixed. The mixture was reacted at 40° C. for 2 hours. The reaction was stopped by adding 5% SDS (0.25 ml) and 1M HCl (0.125 ml), and the absorbance at 345 nm was measured. Water was used as a blank instead of the measurement sample, and a value obtained by subtracting the measured value of the blank was used as DOD. The binding amount of the amino group in the unmodified BO was defined as 8 (7 for lysine and 1 for N-terminal), and the amount of the amino group was quantified.

2. Results

The results of the activity measurement are shown in the following Table 1. The yield was about 50%.

TABLE 1

| Yield of sample (activity value of each sample) | | | | |
|---|---|---|---|---|
| | U/ml | Amount | Total units | Yield (%) |
| Unmodified BO (before reaction) | 2660 | 0.2 g | 532 | 100 |
| Modified BO (after reaction) | 70 | 4 ml | 280 | 52.7 |

The results of the isoelectric focusing are shown in FIG. 1. The untreated sample shows pI4, whereas the corresponding bands disappeared in all of the modified samples (it is considered that the electrical charge was improved). Furthermore, the band was smeared in all of the modified samples. The reason is considered that various BOs having different degrees of modification are present.

The results of the quantification of the amino group are shown in the following Table 2. It is understood that an amino group has been added to the modified BOs.

TABLE 2

| Sample | OD | ΔO. D. | Amino group | OD per one amino group |
|---|---|---|---|---|
| Blank (water) | 0.445 | 0 | — | |
| Unmodified BO | 0.990 | 0.545 | 8.0 | 0.0681 |
| Modified BO | 1.681 | 1.236 | 18.1 | |

It was confirmed from the above-mentioned results that modified BO in which the electrical charge had been changed by addition of an amino group was successfully prepared.

B. Confirmation of Dyeing Effect of Modified BO by Hair Dye Tests

As mentioned above, it was confirmed that the BO as prepared had been modified with an amino group. Therefore, hair dye tests were conducted by using the unmodified BO and modified BO.

1. Process (1) Preparation of Hair Dye Base

2% of EMALEX HC-20 (Nihon-Emulsion Co., Ltd.), 1% of lactic acid and 1% of P-phenylenediamine (PPD) were dissolved in distilled water, and the pH was adjusted to a predetermined pH by using monoethanolamine. Next, 1.5% of hydroxyethyl cellulose was added, mixing was conducted, and the final weight was adjusted by distilled water so as to become 80%. Subsequently, an enzyme was added to adjust the weight so as to finally become 100%.

(2) Hair Dye Test 2 g of the hair dye base was applied per one human white hair bundle (10 cm, 1 g, manufactured by Beaulax). A reaction was conducted at 30° C. for 30 minutes (the bundle was turned at 15 minutes in midstream). The bundle was washed with water and further washed with 1% SDS, and washing with water was conducted until the color disappeared. Finally, the bundle was left overnight and air-dried.

(3) Evaluation of Hue

Using a spectrophotometer CM-700d (manufactured by Konica Minolta, Inc.), a measurement was conducted under a visual field of 10°, D65 Day Light and an SCE mode. Using the CIEL*a*b Color System, an evaluation was made based on the color difference from untreated white hairs (ΔE*ab). L* represents a luminosity value. The value ranges from 0 to 100, and a higher value shows higher luminance. Furthermore, a* represents a color. The value ranges from −60 to +60, and the value closer to − represents stronger green and the value closer to + represents stronger red. b* represents a color. The value ranges from −60 to +60, and the value closer to − represents stronger blue and the value closer to + represents stronger yellow. ΔE*ab is a value calculated by $[(\Delta L)^2 + (\Delta a)^2 + (\Delta b)^2]^{1/2}$, and is a unit that is generally used in the evaluation of hair colors. ΔE*ab is calculated by the difference of criteria values (the measured values of the white hairs before dyeing) from the values of L*, a* and b*. The relationship between the degree of the color difference and ΔE*ab is shown in Table 3. ΔE*ab is about 40 in a general hair manicure, and ΔE*ab is 50 or more in a hair manicure using hydrogen peroxide as an oxidizing agent, but the values vary depending on the condition.

TABLE 3

| Evaluation on degree of color difference | ΔE * ab |
|---|---|
| Quite slightly different | 0-0.5 |
| Slightly different | 0.5-1.5 |
| Difference can be detected | 1.5-3.0 |
| Significantly different | 3.0-6.0 |
| Quite significantly different | 6.0-12.0 |
| Becomes another color system | 12.0 or more |

2. Results (1) Hair Dye Test 1 (Comparison of Dyeing Effects at pH 8 and 9)

Figure 2:
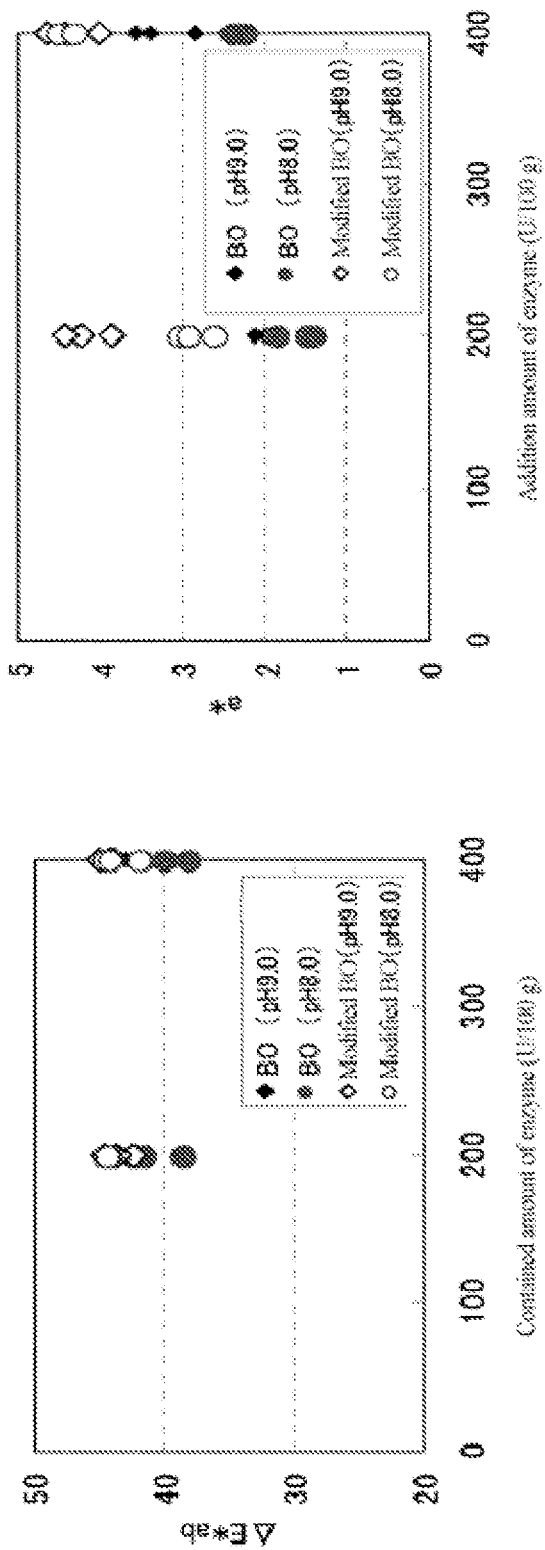
FIG. 2 shows the result of Hair dye test 1. The comparison of the color differences ($\Delta E^*ab$) is shown in the left, and the comparison of the degrees of redness ($a^*$) is shown in the right.

The results of the hair dye test 1 are shown in Table 4 and FIG. 2. Specifically, under the condition of pH 8, the modified BO has a higher dyeing effect (difference of about 3 by color difference). A difference in dyeing effect is observed also under the condition of pH 9.0. The hairs are dyed in stronger red by the modified BO as a whole, and the values of a* (degree of redness) are higher (in the right of FIG. 2). The impression by naked-eye observation was such that the hairs had been dyed better by the modified BO than the numerical values.

TABLE 4

| Sample | | Addition amount (/100 g) | Adjusted pH | ΔE * ab | | | a* (Degree of redness) | | |
|---|---|---|---|---|---|---|---|---|---|
| Control | Without enzyme | — | 9 | 13.8 | 14.8 | 15.6 | 3.1 | 3.3 | 3.2 |
| Condition 1 | BO | 200U | 9 | 44.6 | 41.8 | 43.7 | 2.1 | 2.0 | 2.1 |
| Condition 2 | BO | 400U | 9 | 43.4 | 44.9 | 43.0 | 2.8 | 3.6 | 3.4 |
| Condition 3 | Modified BO | 200U | 9 | 42.5 | 44.6 | 43.6 | 3.9 | 4.2 | 4.4 |
| Condition 4 | Modified BO | 400U | 9 | 45.1 | 43.8 | 44.2 | 4.6 | 4.0 | 4.4 |
| Condition 5 | BO | 200U | 8 | 41.4 | 38.4 | 42.2 | 1.4 | 1.8 | 1.5 |
| Condition 6 | BO | 400U | 8 | 41.7 | 38.1 | 39.8 | 2.4 | 2.2 | 2.3 |
| Condition 7 | Modified BO | 200U | 8 | 44.4 | 44.0 | 44.1 | 3.0 | 2.9 | 2.6 |
| Condition 8 | Modified BO | 400U | 8 | 41.8 | 44.4 | 43.9 | 4.4 | 4.5 | 4.3 |

(2) Hair Dye Test 2 (Comparison of Dyeing Effects at pH 7, 8, 9 and 10 Under Constant Enzyme Concentration)

Figure 3:
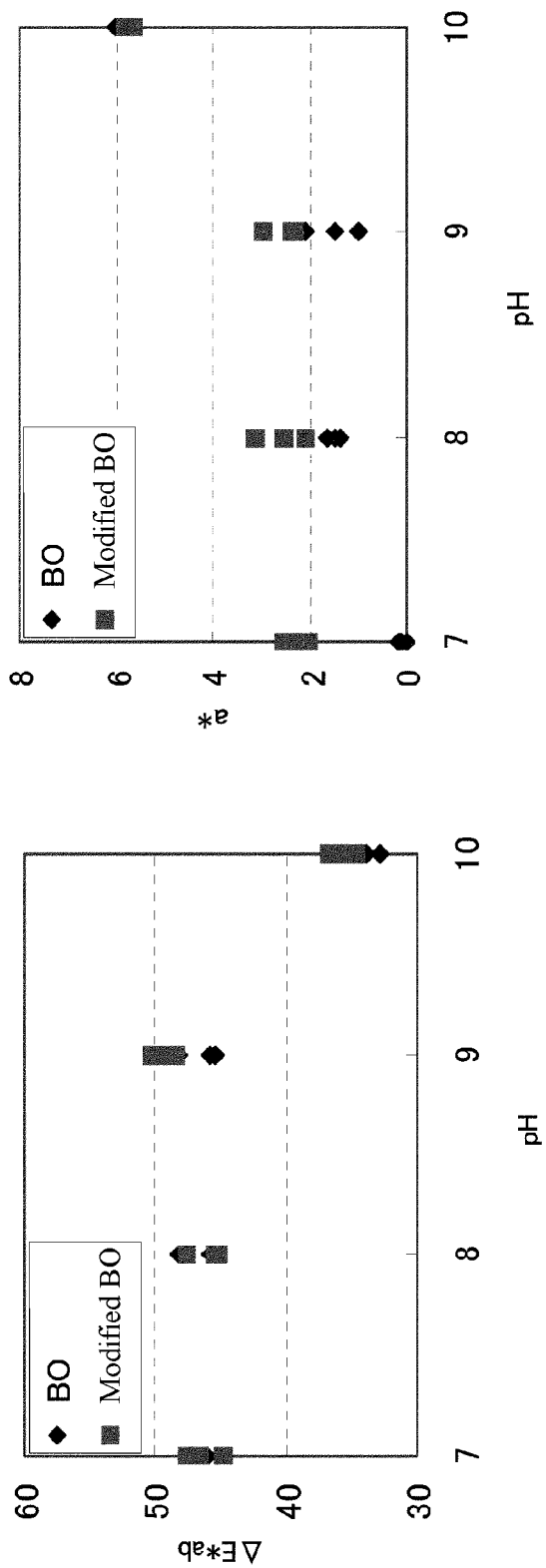
FIG. 3 shows the result of Hair dye test 2 (200 U/100 g). The comparison of the color differences ($\Delta E^*ab$) is shown in the left, and the comparison of the degrees of redness ($a^*$) is shown in the right.

The results of the hair dye test 2 are shown in Table 5 and FIG. 3. Specifically, under the condition of pH 9.0, the modified BOs have higher dyeing effects (the left of FIG. 3). A tendency that the modified BO has a higher a* was shown in either pH (the right in FIG. 3).

TABLE 5

| Sample | | Addition amount (/100 g) | Adjusted pH | ΔE * ab | | | a* (Degree of redness) | | |
|---|---|---|---|---|---|---|---|---|---|
| Control | Without enzyme | — | 9 | 12.2 | 12.2 | 12.2 | 3.1 | 3.3 | 3.2 |
| Condition 1 | BO | 200U | 7 | 45.9 | 45.9 | 47.2 | 0.0 | 0.1 | 0.1 |
| Condition 2 | Modified BO | 200U | 7 | 46.7 | 44.9 | 47.6 | 2.5 | 2.2 | 2.0 |
| Condition 3 | BO | 200U | 8 | 47.7 | 48.3 | 45.9 | 1.6 | 1.5 | 1.4 |
| Condition 4 | Modified BO | 200U | 8 | 45.2 | 47.7 | 45.4 | 2.1 | 2.5 | 3.1 |
| Condition 5 | BO | 200U | 9 | 45.8 | 45.4 | 48.2 | 1.0 | 2.1 | 1.5 |
| Condition 6 | Modified BO | 200U | 9 | 49.1 | 50.2 | 48.5 | 2.9 | 2.4 | 2.3 |

TABLE 5-continued

| Sample | Addition amount (/100 g) | Adjusted pH | ΔE * ab | | | a* (Degree of redness) | | |
|---|---|---|---|---|---|---|---|---|
| Condition 7 | BO | 200U | 10 | 33.9 | 32.9 | 34.2 | 6.0 | 6.0 | 5.9 |
| Condition 8 | Modified BO | 200U | 10 | 34.7 | 35.9 | 36.7 | 5.7 | 5.8 | 5.7 |

(Note: columns above are Sample / Addition amount / Adjusted pH / ΔE*ab (3 values) / a* (3 values))

(3) Hair Dye Test 3 (Comparison of Dyeing Effects at Respective Enzyme Concentrations at pH 8)

Figure 4:
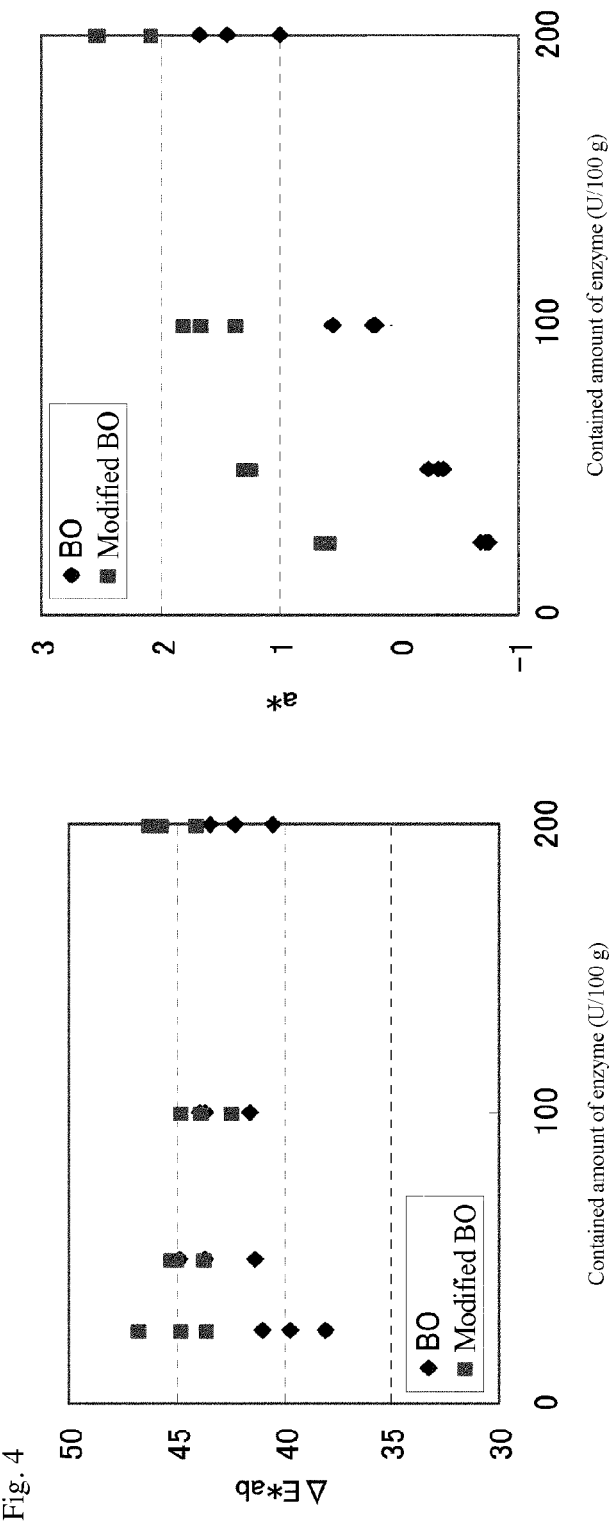
FIG. 4 shows the result of Hair dye test 3 (pH 8.0). The comparison of the color differences ($\Delta E^*ab$) is shown in the left, and the comparison of the degrees of redness ($a^*$) is shown in the right.

The results of the hair dye test 3 are shown in Table 6 and FIG. 4. The modified BO showed a high dyeing effect even under a condition of a low enzyme concentration (the left of FIG. 4). Furthermore, it was confirmed that the modified BO had a higher degree of redness also in this test.

TABLE 6

| | Sample | Addition amount (/100 g) | Adjusted pH | ΔE * ab | | | a* (Degree of redness) | | |
|---|---|---|---|---|---|---|---|---|---|
| Control | Without enzyme | — | 8 | 13.5 | 11.4 | 10.1 | 3.39 | 3.14 | 2.88 |
| Condition 1 | BO | 25U | 8 | 39.7 | 41.0 | 38.1 | −0.72 | −0.74 | −0.69 |
| Condition 2 | Modified BO | 25U | 8 | 43.6 | 44.8 | 46.8 | 0.57 | 0.65 | 0.57 |
| Condition 3 | BO | 50U | 8 | 43.7 | 44.9 | 41.3 | −0.25 | −0.33 | −0.37 |
| Condition 4 | Modified BO | 50U | 8 | 45.0 | 45.2 | 43.7 | 1.28 | 1.24 | 1.3 |
| Condition 5 | BO | 100U | 8 | 43.6 | 41.6 | 43.9 | 0.22 | 0.2 | 0.56 |
| Condition 6 | Modified BO | 100U | 8 | 42.4 | 43.8 | 44.8 | 1.8 | 1.66 | 1.35 |
| Condition 7 | BO | 200U | 8 | 42.3 | 40.5 | 43.4 | 1.44 | 0.99 | 1.67 |
| Condition 8 | Modified BO | 200U | 8 | 46.3 | 44.0 | 45.7 | 2.07 | 2.54 | 2.51 |

(4) Hair Dye Test 4 (Comparison of Respective Enzyme Concentrations and Substrate-Specific Dyeing Effects at pH 9)

Figure 5:
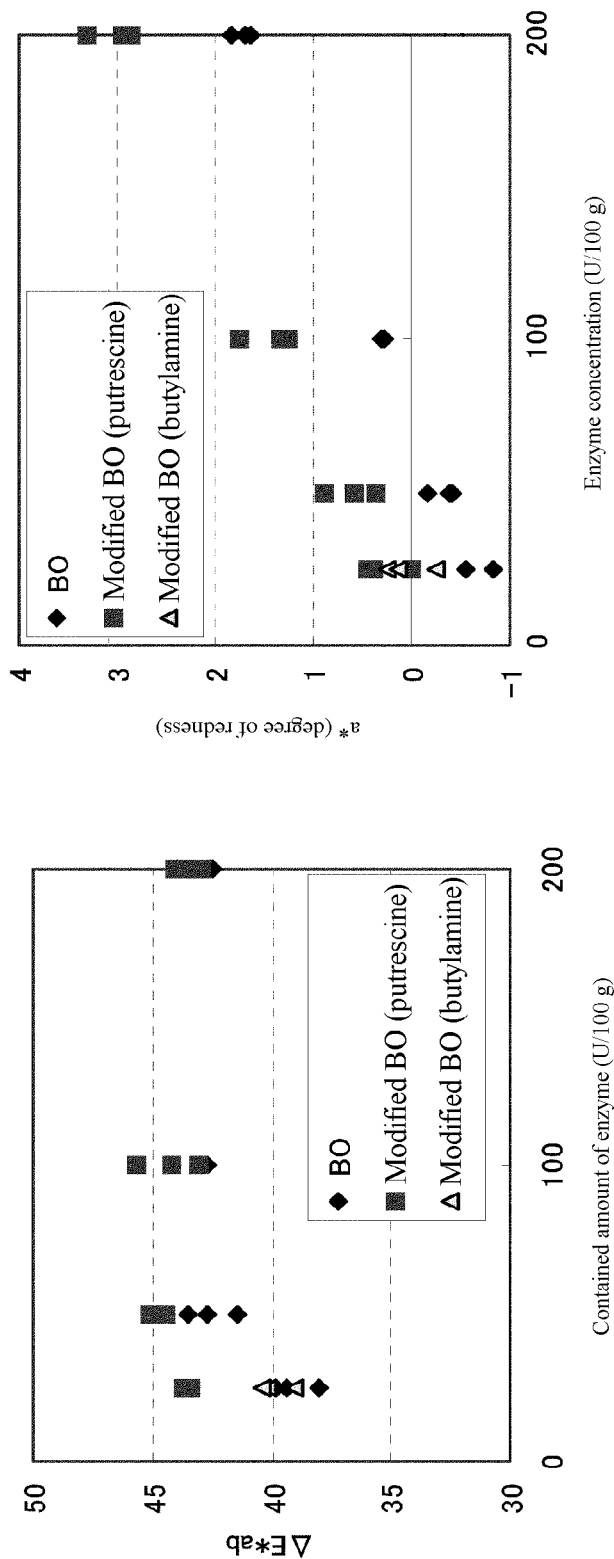
FIG. 5 shows the result of Hair dye test 4 (pH 9.0). The comparison of the color differences ($\Delta E^*ab$) is shown in the left, and the comparison of the degrees of redness ($a^*$) is shown in the right.
Figure 6:
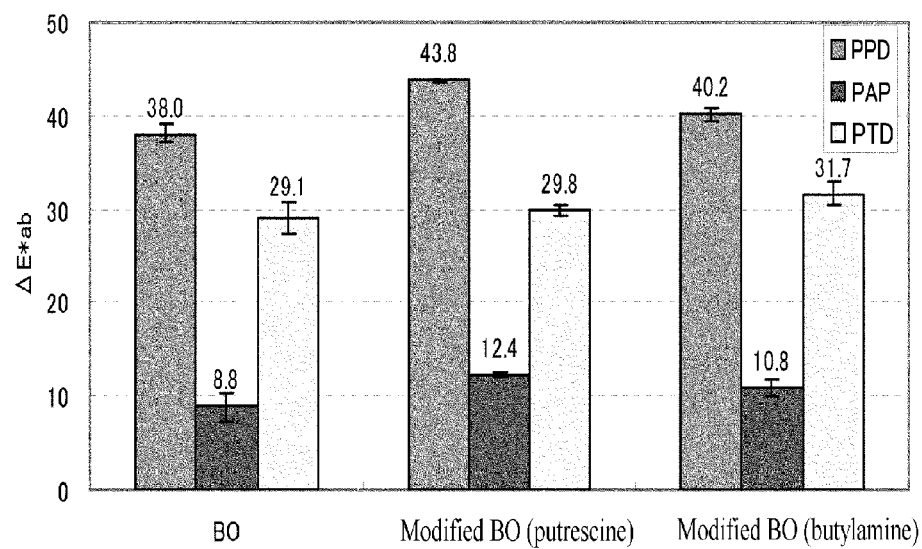
FIG. 6 shows the comparison of the substrate specificities of the various modified BOs (pH 9.0, 25 U/100 g). The dyeing properties in the cases when different chromogenic substrates (dyeing substrates) were used were compared. PPD: paraphenylenediamine, PAP: paraminophenol, PTD: paratoluenediamine

The dyeing effects were also examined for PAP (paraminophenol) and PTD (paratoluenediamine) besides PPD (paraphenylenediamine) as chromogenic substrates (consideration of substrate specificity). Furthermore, an enzyme modified by using butylamine was newly prepared, and the dyeing effect thereof is similarly compared. The results are shown in Table 7 and FIGS. 5 and 6. It can be confirmed that the modified BO (putrescine) shows a high dyeing effect under a condition of pH 9.0 (the left of FIG. 5). Furthermore, the modified BO (putrescine) showed a tendency of a high degree of redness. With respect to substrate specificity, the BO modified with putrescine has a higher dyeing effect on PPD and PAP as compared to that of the unmodified BO (FIG. 6). Furthermore, the BO modified with butylamine showed a tendency of a higher dyeing effect specifically on PTD (FIG. 6).

TABLE 7

| | Sample | Addition amount (/100 g) | Substrate | Adjusted pH | ΔE * ab | | | a* (Degree of redness) | | |
|---|---|---|---|---|---|---|---|---|---|---|
| Condition 1 | Without enzyme | — | PPD | 9 | 7.5 | 7.1 | | 3.74 | 3.62 | |
| Condition 2 | Butylamine BO | 25U | PPD | 9 | 40.2 | 39.1 | 40.4 | −0.26 | 0.25 | 0.13 |
| Condition 3 | BO | 25U | PPD | 9 | 38.0 | 39.9 | 39.4 | −0.84 | −0.56 | −0.56 |
| Condition 4 | Putrescine BO | 25U | PPD | 9 | 43.8 | 43.4 | 43.7 | 0.44 | 0 | 0.4 |
| Condition 5 | BO | 50U | PPD | 9 | 42.6 | 43.5 | 41.4 | −0.39 | −0.17 | −0.41 |
| Condition 6 | Putrescine BO | 50U | PPD | 9 | 45.1 | 44.4 | 45.0 | 0.57 | 0.35 | 0.89 |
| Condition 7 | BO | 100U | PPD | 9 | 43.0 | 44.2 | 42.7 | 0.27 | 0.29 | 0.3 |
| Condition 8 | Putrescine BO | 100U | PPD | 9 | 45.7 | 44.2 | 43.1 | 1.74 | 1.24 | 1.32 |
| Condition 9 | BO | 200U | PPD | 9 | 42.6 | 42.4 | 43.9 | 1.82 | 1.7 | 1.65 |
| Condition 10 | Putrescine BO | 200U | PPD | 9 | 42.9 | 43.3 | 44.1 | 2.85 | 3.3 | 2.94 |
| Condition 11 | BO | 25U | PAP | 9 | 8.8 | 10.1 | 7.0 | 6.56 | 6.9 | 5.97 |
| Condition 12 | BO | 25U | PTP | 9 | 28.9 | 26.1 | 29.1 | 3.44 | 3.26 | 3.33 |
| Condition 13 | Putrescine BO | 25U | PAP | 9 | 12.4 | 13.0 | 12.9 | 7.18 | 6.96 | 7.29 |
| Condition 14 | Putrescine BO | 25U | PTP | 9 | 30.0 | 28.9 | 29.8 | 3.56 | 3.35 | 3.37 |
| Condition 15 | Butylamine BO | 25U | PAP | 9 | 10.8 | 9.7 | 11.4 | 6.86 | 6.42 | 6.67 |
| Condition 16 | Butylamine BO | 25U | PTP | 9 | 32.8 | 30.4 | 31.7 | 4.81 | 4.81 | 5.36 |
| Condition 17 | Without enzyme | — | PAP | 9 | 5.5 | 5.0 | | 4.65 | 4.73 | |
| Condition 18 | Without enzyme | — | PTP | 9 | 8.7 | 10.0 | | 5.07 | 5.75 | |

As mentioned above, it was shown that the modified BO has a higher dyeing effect than that of the unmodified BO. The difference in the dyeing effect was specifically significant at low enzyme concentrations. Furthermore, it was clarified that the modified BO had stronger redness than that of the unmodified BO. It is considered that the pH of hairs is about 5.5, and hairs are negatively charged under a general dyeing condition (for example, pH 9.0). It is thought that the modified BO that has been positively (+) charged is present even under a condition of pH 9.0, as a result of the improved charge of the BO by the modification of the BO with an amino group. It is thought that the affinity for the hairs was improved by the effect of the charge in the modified BO, and consequently the dyeing effect was improved.

C. Confirmation of Dyeing Effects by Various Modification Processes

BO was modified by using various polyamines, and the dyeing effects were compared.

1. Process (1) Modification with Amino Group 1,000 equivalent amount of a polyamine (putrescine, 3,3'-diaminodipropylamine, agmatine sulfate), 100 equivalent amount of N-hydroxysuccinimide and 200 equivalent amount of water-soluble carbodiimide (EDC) on the basis of molar ratio were added to 100 mg of BO, adjusted to 10 ml with 20 mM HEPES (pH 6.5), and reacted at 4° C. for 1 day. The pHs of the putrescine and 3,3'-diaminodipropylamine were adjusted with diluted sulfuric acid.

(2) Purification of Sample

In order to remove the unreacted polyamine from the sample after the reaction, the sample was purified by a 10DG column (BIO-RAD) that had been equilibrated with a 20 mM borate buffer solution (pH 9.0).

(3) Measurement of Activity

A measurement method by the change in absorbance at a wavelength of 460 nm using bilirubin as a substrate was used.

(4) Isoelectric Focusing

In order to compare the electrical charge with that of unmodified BO, isoelectric focusing was conducted.

(5) Quantification of Amino Group

The amino group was quantified by using TNBS.

(6) Quantification of Protein

The protein amount was quantified by the Bradford method. BSA was used as a standard.

(7) Shampoo Resistance Test (Fastness Test)

A dyed hair bundle was immersed in a 10 vol % solution of EMAL 20C (Kao Corporation), and a sonication treatment was conducted for 30 minutes. Thereafter the hair bundle was washed thoroughly with water and dried, and the color difference was measured. The shampoo resistance was represented by the color difference of the hairs after washing with respect to the color difference of the hairs before washing (%).

2. Results (1) Modification Reaction, Isoelectric Focusing, Measurement of Specific Activity and Quantification of Amino Groups With respect to the modification reaction, the yields of the respective samples are shown in Table 8. The yields were 30% to 50%.

TABLE 8

| Sample | (U/ml) | Amount | Total units | Yield (%) |
|---|---|---|---|---|
| BO | 2660 | 100 mg | 266 | 100 |
| Diamine (putrescine) | 35 | 4 ml | 140 | 53 |
| Triamine (3,3'-diaminodipropylamine) | 26 | 4 ml | 104 | 39 |
| Tetraamine (agmatine sulfate) | 20 | 4 ml | 80 | 30 |

Figure 7:
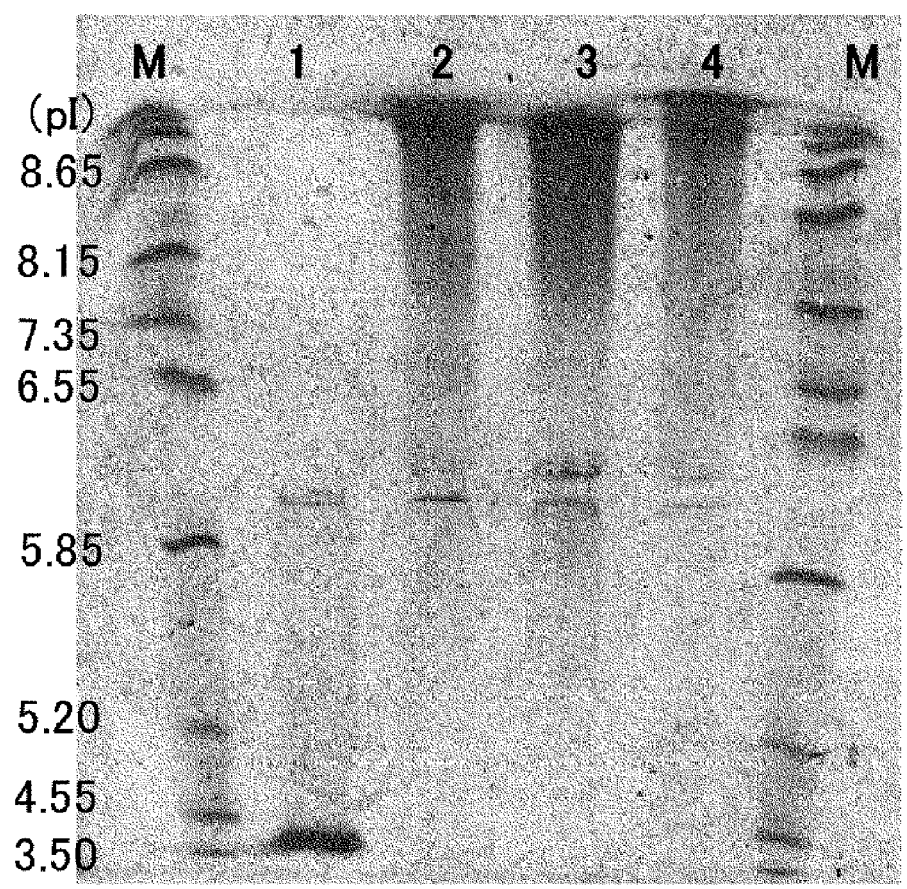
FIG. 7 shows the results of the isoelectric focusing for the various modified BOs. Lane 1: unmodified BO, Lane 2: diamine (putrescine)-modified BO, Lane 3: triamine (3,3'-diaminodipropylamine)-modified BO, Lane 4: tetraamine (agmatine sulfate)-modified BO, Lane M: molecular weight marker.

The results of the isoelectric focusing are shown in FIG. 7. The untreated sample showed pI 4, whereas the charge was improved in all of the modified samples.

The measurement results of the specific activities are shown in Table 9. The specific activities became about half by the modification.

TABLE 9

| Sample | Activity (U/ml) | Protein amount (mg/ml) | Specific activity (U/mg) |
|---|---|---|---|
| Unmodified BO | 19 | 1.90 | 10.0 |
| Diamine-modified BO | 35 | 4.52 | 7.7 |
| Triamine-modified BO | 26 | 5.94 | 4.3 |
| Tetraamine-modified BO | 20 | 3.99 | 5.0 |

The results of the quantification of the amino group are shown in Table 10. It can be confirmed that the amino group has been added to the modified BO.

TABLE 10

| Sample | OD | Blank | ΔO. D. | Amino groups | OD per one amino group |
|---|---|---|---|---|---|
| Unmodified BO | 0.99 | 0.445 | 0.545 | 8 | 0.0681 |
| Diamine-modified BO | 2.14 | 0.445 | 1.696 | 25 | |
| Triamine-modified BO | 4.11 | 0.445 | 3.665 | 54 | |
| Tetraamine-modified BO | 1.40 | 0.445 | 0.955 | 14 | |

(2) Confirmation of Dyeing Effects by Hair Dye Tests

Figure 8:
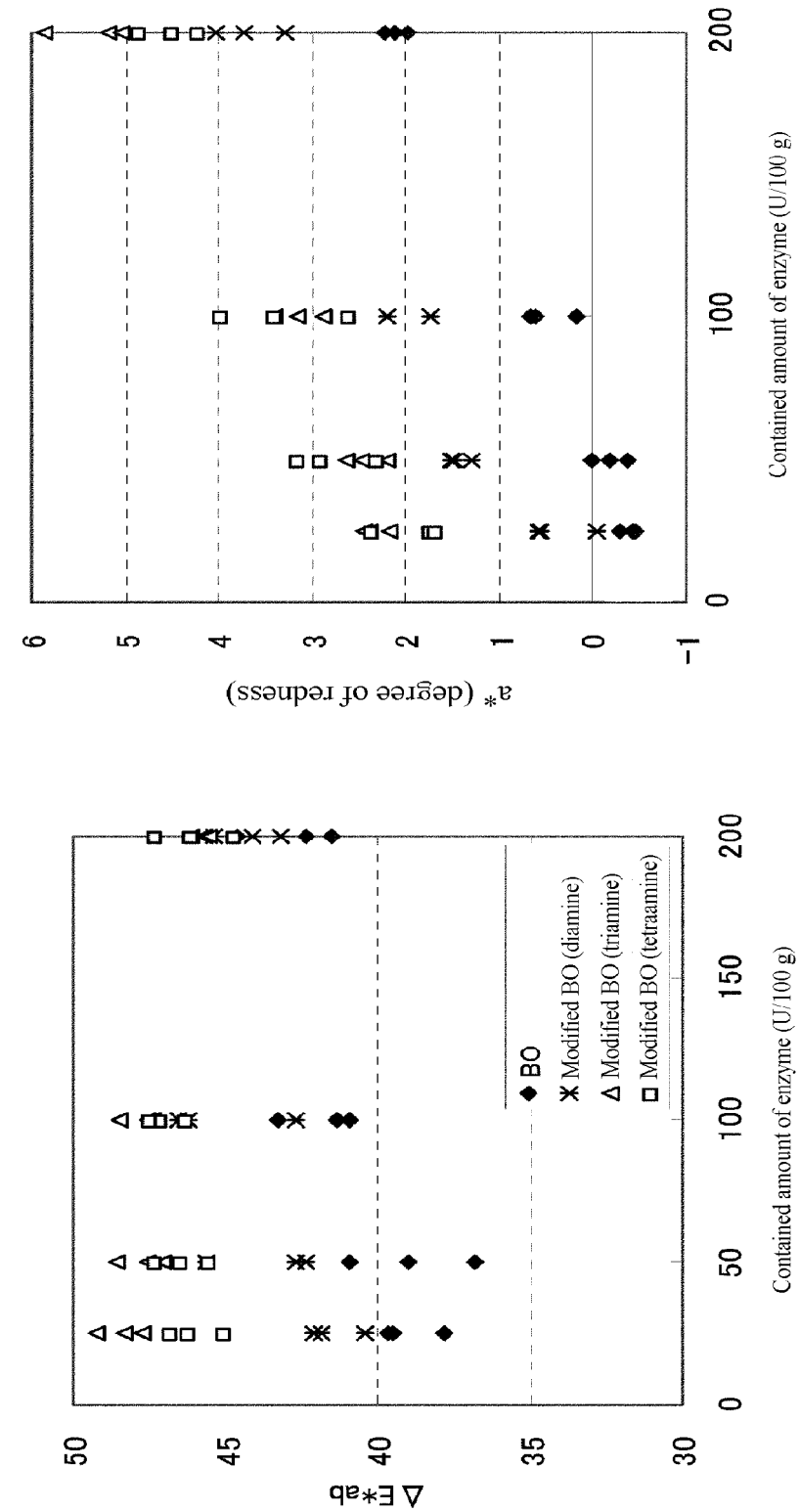
FIG. 8 shows the comparison of the dyeing effects by the various modified BOs (pH 9.0). The comparison of the color differences ($\Delta E^*ab$) is shown in the left, and the comparison of the degrees of redness ($a^*$) is shown in the right.
Figure 9:
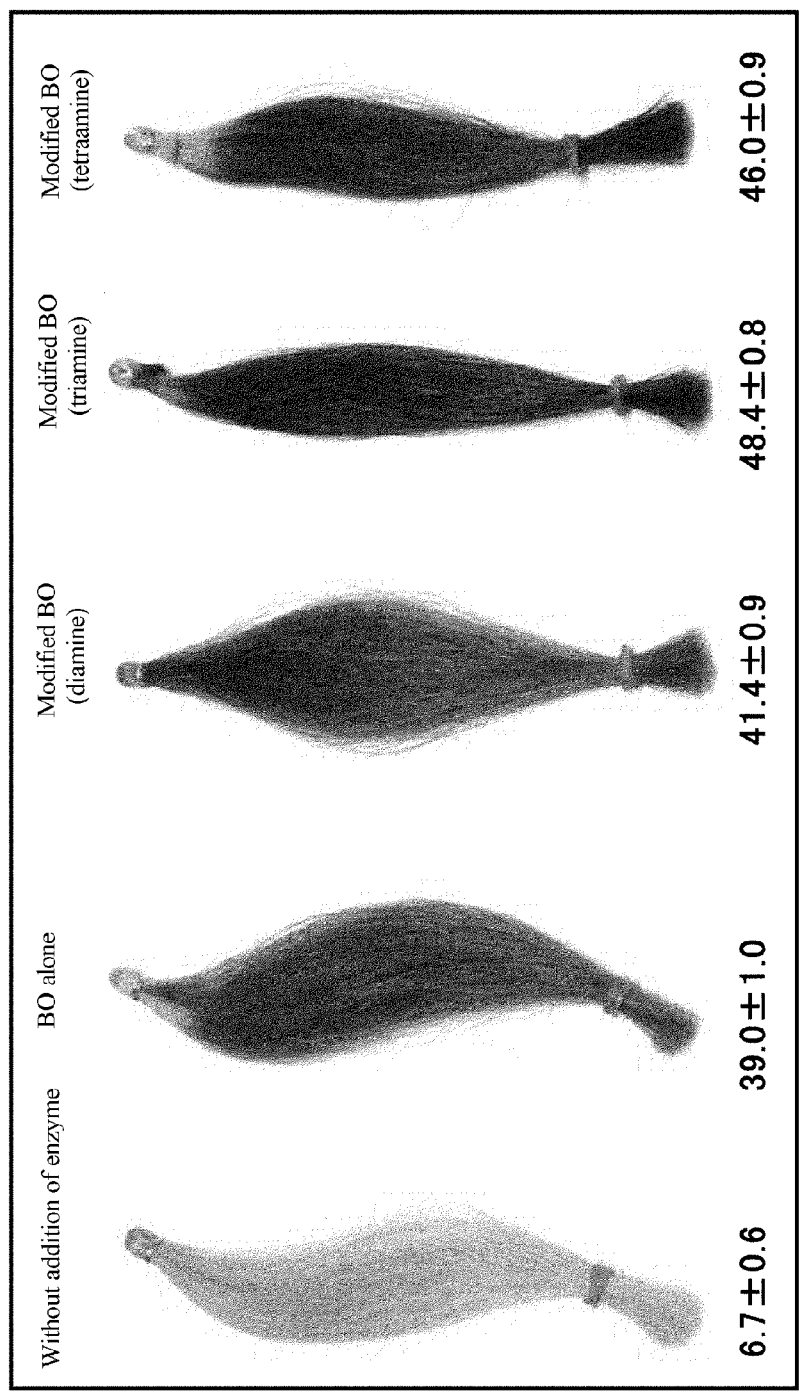
FIG. 9 shows the comparison of the dyeing effects by the various modified BOs (pH 9.0). The drawing shows the comparison of the dyed hairs for the various modified BOs. The amounts of the enzymes were set to be constant, 25 U/100 g. The values show color differences from white hairs ($\Delta E^*ab$) (n=3). A higher value shows a higher dyeing effect.

Hair dye tests were conducted on the prepared respective modified BOs. The method and evaluation are similar to those of the case of B. However, the dyeing was conducted under a condition of pH 9.0 in all cases. The results of the hair dye test are shown in Table 11 and FIGS. 8 and 9. It is understood that a high dyeing effect can be obtained by modifying a polyamine. Specifically, the hair dyeing effect was the highest in the modified triamine (the left of FIG. 8). Since the maximum color difference was shown at the lowest enzyme concentration, it is expected that the dyeing effect is further improved by decreasing the enzyme concentration.

TABLE 11

| | Sample | Addition amount (/100 g) | ΔE * ab | | | a* (Degree of redness) | | |
|---|---|---|---|---|---|---|---|---|
| Control | Without enzyme | — | 7.2 | 6.1 | 7.0 | 4.0 | 3.8 | 3.6 |
| Condition 1 | Unmodified BO | 25U | 39.5 | 39.7 | 37.9 | −0.4 | −0.3 | −0.5 |
| Condition 2 | Unmodified BO | 50U | 39.0 | 36.8 | 40.9 | −0.4 | −0.2 | 0.0 |
| Condition 3 | Unmodified BO | 100U | 40.9 | 41.3 | 43.3 | 0.2 | 0.6 | 0.7 |
| Condition 4 | Unmodified BO | 200U | 42.3 | 44.6 | 41.5 | 2.1 | 2.0 | 2.2 |
| Condition 5 | Diamine-modified BO | 25U | 40.4 | 42.1 | 41.8 | 0.0 | 0.6 | 0.6 |
| Condition 6 | Diamine-modified BO | 50U | 45.6 | 42.3 | 42.7 | 1.5 | 1.3 | 1.5 |
| Condition 7 | Diamine-modified BO | 100U | 42.7 | 46.3 | 46.6 | 2.2 | 2.2 | 1.7 |
| Condition 8 | Diamine-modified BO | 200U | 45.4 | 44.1 | 43.2 | 3.7 | 4.0 | 3.3 |
| Condition 9 | Triamine-modified BO | 25U | 49.3 | 47.8 | 48.3 | 2.4 | 2.2 | 2.5 |
| Condition 10 | Triamine-modified BO | 50U | 47.1 | 47.6 | 48.5 | 2.2 | 2.5 | 2.6 |
| Condition 11 | Triamine-modified BO | 100U | 48.5 | 47.5 | 47.4 | 3.2 | 3.4 | 2.9 |
| Condition 12 | Triamine-modified BO | 200U | 45.7 | 46.2 | 45.5 | 5.9 | 5.2 | 5.1 |
| Condition 13 | Tetraamine-modified BO | 25U | 45.0 | 46.8 | 46.2 | 1.7 | 2.4 | 1.7 |
| Condition 14 | Tetraamine-modified BO | 50U | 46.5 | 47.3 | 45.6 | 2.3 | 3.2 | 2.9 |
| Condition 15 | Tetraamine-modified BO | 100U | 46.3 | 47.1 | 47.5 | 2.6 | 4.0 | 3.4 |
| Condition 16 | Tetraamine-modified BO | 200U | 44.7 | 47.3 | 46.1 | 4.2 | 4.8 | 4.5 |

(3) Results of Shampoo Resistance Tests

Figure 10:
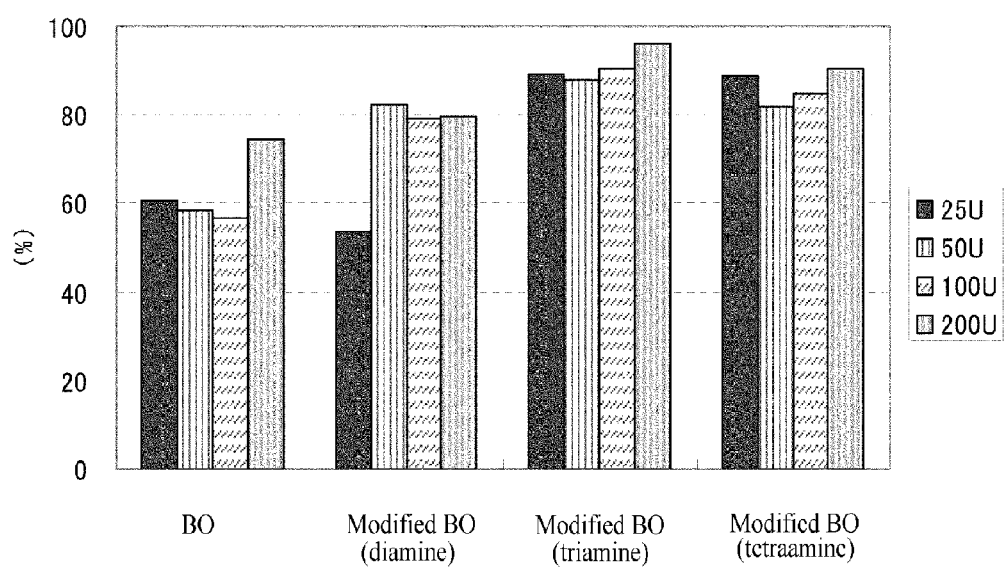
FIG. 10 shows the results of the shampoo resistance tests. The shampoo resistances were compared by using the color difference of the hairs after washing with respect to the color difference of the hairs before washing (%).
Figure 11:
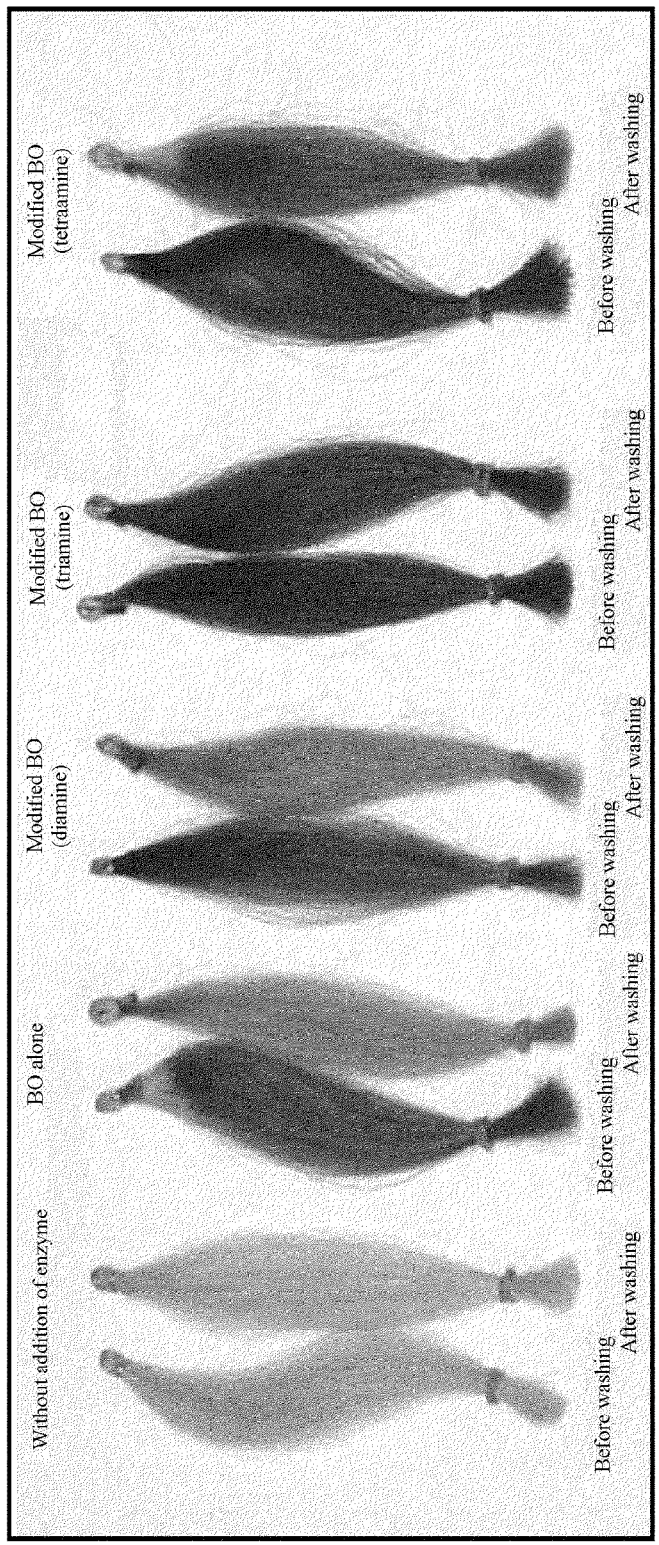
FIG. 11 shows the results of the shampoo resistance tests. The comparison of the hairs before and after washing is shown for the various modified BOs. The amounts of the enzymes were set to be constant, 25 U/100 g.

The results of the shampoo resistance tests are shown in Table 12 and FIGS. 10 and 11. The dyeing by the modified BO was excellent in shampoo resistance, and showed a tendency that color loss was more difficult to occur than that in the case when the unmodified BO was used. This characteristic of the modified BO is extremely important and significant in use for hair dyeing.

TABLE 12

| | Sample | Addition amount (/100 g) | Before washing ΔE Aver. | After washing ΔE Aver. | Ratio (%) |
|---|---|---|---|---|---|
| Control | Without enzyme | — | 6.7 | 5.3 | 77.9 |
| Condition 1 | Unmodified BO | 25 U | 39.0 | 23.6 | 60.5 |
| Condition 2 | Unmodified BO | 50 U | 38.9 | 22.7 | 58.4 |
| Condition 3 | Unmodified BO | 100 U | 41.9 | 23.7 | 56.5 |
| Condition 4 | Unmodified BO | 200 U | 42.8 | 32.0 | 74.6 |
| Condition 5 | Diamine-modified BO | 25 U | 41.4 | 22.2 | 53.7 |
| Condition 6 | Diamine-modified BO | 50 U | 43.5 | 35.8 | 82.2 |
| Condition 7 | Diamine-modified BO | 100 U | 45.2 | 35.8 | 79.3 |
| Condition 8 | Diamine-modified BO | 200 U | 44.2 | 35.1 | 79.5 |
| Condition 9 | Triamine-modified BO | 25 U | 48.4 | 43.3 | 89.4 |
| Condition 10 | Triamine-modified BO | 50 U | 47.7 | 41.9 | 87.8 |
| Condition 11 | Triamine-modified BO | 100 U | 47.8 | 43.4 | 90.7 |
| Condition 12 | Triamine-modified BO | 200 U | 45.8 | 44.0 | 96.0 |
| Condition 13 | Tetraamine-modified BO | 25 U | 46.0 | 40.9 | 88.9 |
| Condition 14 | Tetraamine-modified BO | 50 U | 46.5 | 38.0 | 81.8 |
| Condition 15 | Tetraamine-modified BO | 100 U | 47.0 | 39.9 | 84.8 |
| Condition 16 | Tetraamine-modified BO | 200 U | 46.0 | 41.6 | 90.4 |

N = 3
N = 2

As mentioned above, it was possible to dramatically improve the hair dyeing effect by changing the polyamine used for the modification. Furthermore, it was clarified that the modified BO also improves the shampoo resistance besides the dyeing effect.

D. Dyeing Effects in Cases when Indole Analogues are Used as Chromogenic Substrates 1

The dyeing effects in the cases when indole compounds (4-aminoindole, 5-aminoindole and the like), which are considered to be safer than paraphenylenediamine and the like, are used as chromogenic substrates, were examined.

1. Process (1) Modification with Amino Group 1,000 equivalent amount of 3,3'-diaminodipropylamine, 100 equivalent amount of N-hydroxysuccinimide and 200 equivalent amount of water-soluble carbodiimide (EDC) on the basis of molar ratio were added to 100 mg of BO, adjusted to 10 ml with 20 mM HEPES (pH 6.5), and reacted at 4° C. for 1 day. This reaction liquid was purified and used as PMO (Polyamine Modified Oxidase). After the addition of 3,3'-diaminodipropylamine, the pH was adjusted with diluted sulfuric acid.

The test method and evaluation were similar to those in the case of B, except that the above-mentioned PMO was used as the modified BO and an indole compound was used as the chromogenic substrate (in some conditions, two kinds of chromogenic substrates were used in combination). Furthermore, shampoo resistance tests were also conducted by a similar method to that in the case of C.

2. Results (1) Confirmation of Dyeing Effects by Hair Dye Tests

Figure 12:
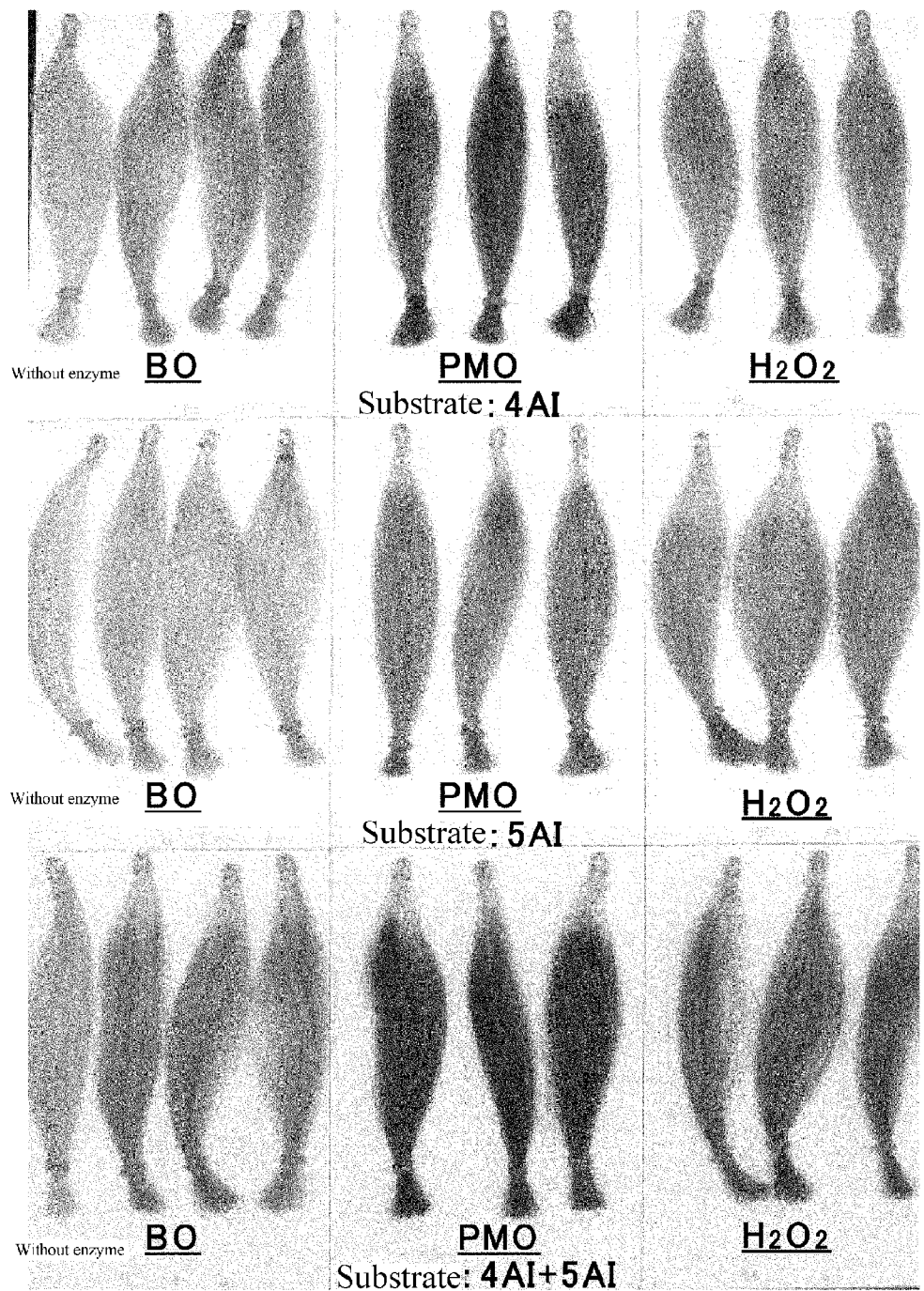
FIG. 12 shows the result of the dyeing tests using indole compounds as chromogenic substrates. The values in the cases when dyed under a condition of pH 7 were compared for BO and PMO, and the values in the cases when dyed under a condition of pH 9 were compared for $H_2O_2$. BO: unmodified enzyme, PMO: modified enzyme, $H_2O_2$: hydrogen peroxide, 4AI: 4-aminoindole, 5AI: 5-aminoindole.

The test results are shown in Table 13 and FIG. 12. It was confirmed that the hair dyeing effect was significantly higher than that of the cases when an unmodified BO or hydrogen peroxide was used, due to addition of PMO. It was possible to change the color to a color close to black by mixing 4AI or 5AI (FIG. 12).

TABLE 13

| | Substrate 1 | Substrate 2 | Oxidizing agent | Concentration | pH | ΔE * ab | | | ΔE * ab (Aver.) | Standard deviation |
|---|---|---|---|---|---|---|---|---|---|---|
| Control | 4AI: 1% | — | — | — | 7 | 3.1 | 4.8 | — | 3.9 | 1.2 |
| Control | 5AI: 1% | — | — | — | 7 | 7.9 | 7.2 | — | 7.6 | 0.5 |
| Control | 5AI: 1% | — | — | — | 9 | 6.3 | 7.0 | — | 6.7 | 0.5 |
| Control | 4AI: 0.5% | 5AI: 0.5% | — | — | 7 | 4.8 | 5.0 | — | 4.9 | 0.1 |
| Control | 4AI: 0.5% | 5AI: 0.5% | — | — | 9 | 4.9 | 4.7 | — | 4.8 | 0.2 |
| Condition 1 | 4AI: 1% | — | BO3 | 25U/100 g | 7 | 20.5 | 20.2 | 22.0 | 20.9 | 1.0 |
| Condition 2 | 4AI: 1% | — | BO3 | 25U/100 g | 9 | 17.8 | 19.8 | 18.0 | 18.5 | 1.1 |
| Condition 3 | 4AI: 1% | — | PMO | 25U/100 g | 7 | 40.0 | 38.2 | 38.5 | 38.9 | 0.9 |
| Condition 4 | 4AI: 1% | — | PMO | 25U/100 g | 9 | 40.0 | 38.9 | 39.7 | 39.5 | 0.6 |
| Condition 5 | 4AI: 1% | — | $H_2O_2$ | 3% | 9 | 23.3 | 21.6 | 22.8 | 22.6 | 0.9 |
| Condition 6 | 5AI: 1% | — | BO3 | 25U/100 g | 7 | 9.4 | 10.2 | 10.0 | 9.8 | 0.4 |
| Condition 7 | 5AI: 1% | — | BO3 | 25U/100 g | 9 | 7.7 | 8.3 | 9.0 | 8.3 | 0.6 |
| Condition 8 | 5AI: 1% | — | PMO | 25U/100 g | 7 | 28.1 | 26.5 | 26.2 | 26.9 | 1.0 |
| Condition 9 | 5AI: 1% | — | PMO | 25U/100 g | 9 | 24.9 | 29.0 | 27.5 | 27.1 | 2.1 |
| Condition 10 | 5AI: 1% | — | $H_2O_2$ | 3% | 9 | 26.4 | 27.2 | 25.4 | 26.3 | 0.9 |
| Condition 11 | 4AI: 0.5% | 5AI: 0.5% | BO3 | 25U/100 g | 7 | 22.8 | 22.3 | 22.9 | 22.7 | 0.3 |
| Condition 12 | 4AI: 0.5% | 5AI: 0.5% | BO3 | 25U/100 g | 9 | 14.4 | 16.1 | 14.3 | 15.0 | 1.0 |
| Condition 13 | 4AI: 0.5% | 5AI: 0.5% | PMO | 25U/100 g | 7 | 40.4 | 42.8 | 39.8 | 41.0 | 1.6 |
| Condition 14 | 4AI: 0.5% | 5AI: 0.5% | PMO | 25U/100 g | 9 | 36.2 | 36.6 | 37.1 | 36.6 | 0.5 |
| Condition 15 | 4AI: 0.5% | 5AI: 0.5% | $H_2O_2$ | 3% | 9 | 32.8 | 32.4 | 31.8 | 32.3 | 0.5 |

4AI: 4-aminoindole
5AI: 5-aminoindole (2) Results of Shampoo Resistance Tests

Figure 13:
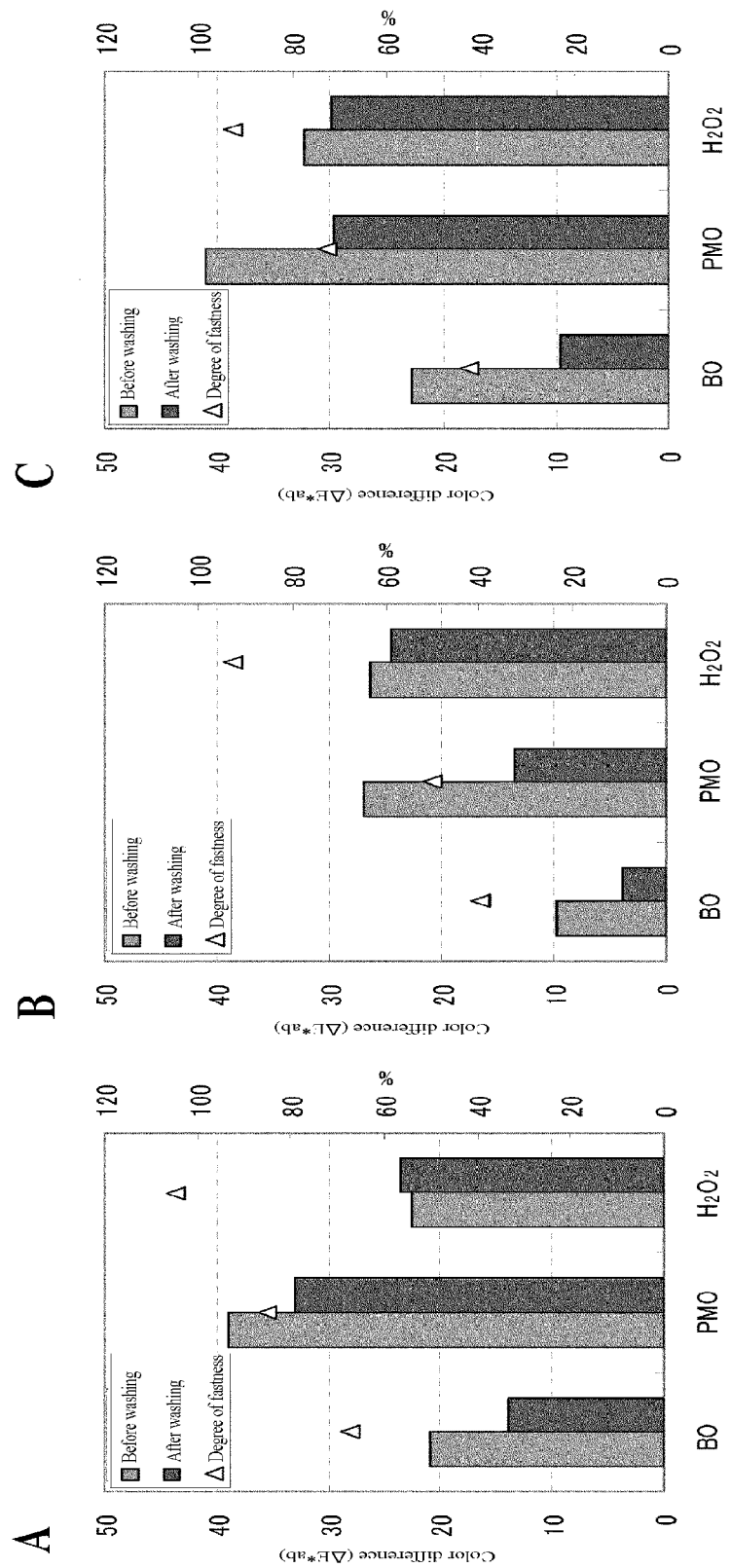
FIG. 13 shows the results of the shampoo resistance tests. The hairs were dyed by using indole compounds as chromogenic substrates, and thereafter washed. The shampoo resistances (degrees of fastness) were compared and evaluated for BO (unmodified enzyme), PMO (modified enzyme) and $H_2O_2$ (hydrogen peroxide). The values in the cases when dyed under a condition of pH 7 were compared for BO and PMO, and the values in the cases when dyed under a condition of pH 9 were compared for $H_2O_2$. A: the result in the case when 4-aminoindole was used as a chromogenic substrate, B: the result in the case when 5-aminoindole was used as a chromogenic substrate, and C: the result in the case when 4-aminoindole and 5-aminoindole were used as chromogenic substrates.

The test results are shown in Table 14 and FIG. 13. PMO had a more excellent hair dyeing effect and lower color loss (higher fastness) than those of unmodified BO. On the other hand, the fastness tended to become higher in the order of 4AI>4AI+5AI>5AI.

TABLE 14

| | Substrate 1 | Substrate 2 | Oxidizing agent | Concentration | pH | ΔE * ab (Aver. before washing) | ΔE * ab (Aver. after washing) | Degree of fastness (%) |
|---|---|---|---|---|---|---|---|---|
| Condition 1 | 4AI: 1% | — | BO3 | 25U/100 g | 7 | 20.9 | 14.0 | 67.1 |
| Condition 2 | 4AI: 1% | — | BO3 | 25U/100 g | 9 | 18.5 | 11.7 | 63.4 |
| Condition 3 | 4AI: 1% | — | PMO | 25U/100 g | 7 | 38.9 | 33.0 | 84.8 |
| Condition 4 | 4AI: 1% | — | PMO | 25U/100 g | 9 | 39.5 | 34.2 | 86.5 |
| Condition 5 | 4AI: 1% | — | $H_2O_2$ | 3% | 9 | 22.6 | 23.7 | 104.9 |
| Condition 6 | 5AI: 1% | — | BO3 | 25U/100 g | 7 | 9.8 | 3.9 | 39.7 |
| Condition 7 | 5AI: 1% | — | BO3 | 25U/100 g | 9 | 8.3 | 3.5 | 42.3 |
| Condition 8 | 5AI: 1% | — | PMO | 25U/100 g | 7 | 26.9 | 13.5 | 50.1 |
| Condition 9 | 5AI: 1% | — | PMO | 25U/100 g | 9 | 27.1 | 15.8 | 58.1 |
| Condition 10 | 5AI: 1% | — | $H_2O_2$ | 3% | 9 | 26.3 | 24.4 | 92.6 |
| Condition 11 | 4AI: 0.5% | 5AI: 0.5% | BO3 | 25U/100 g | 7 | 22.7 | 9.6 | 42.3 |
| Condition 12 | 4AI: 0.5% | 5AI: 0.5% | BO3 | 25U/100 g | 9 | 15.0 | 7.7 | 51.4 |
| Condition 13 | 4AI: 0.5% | 5AI: 0.5% | PMO | 25U/100 g | 7 | 41.0 | 29.8 | 72.6 |
| Condition 14 | 4AI: 0.5% | 5AI: 0.5% | PMO | 25U/100 g | 9 | 36.6 | 27.3 | 74.5 |
| Condition 15 | 4AI: 0.5% | 5AI: 0.5% | $H_2O_2$ | 3% | 9 | 32.3 | 30.0 | 92.7 |

E. Dyeing Effects in Cases when Indole Analogues are Used as Chromogenic Substrates 2

The relationship between the enzyme concentration and dyeing effect, and the dyeing effect in the case when two or more kinds of indole compounds were used in combination were examined.

1. Process

PMO was used as a modified enzyme. Other process and the like were similar to those in the case of D.

2. Results (1) Results of Hair Dye Test

Figure 14:
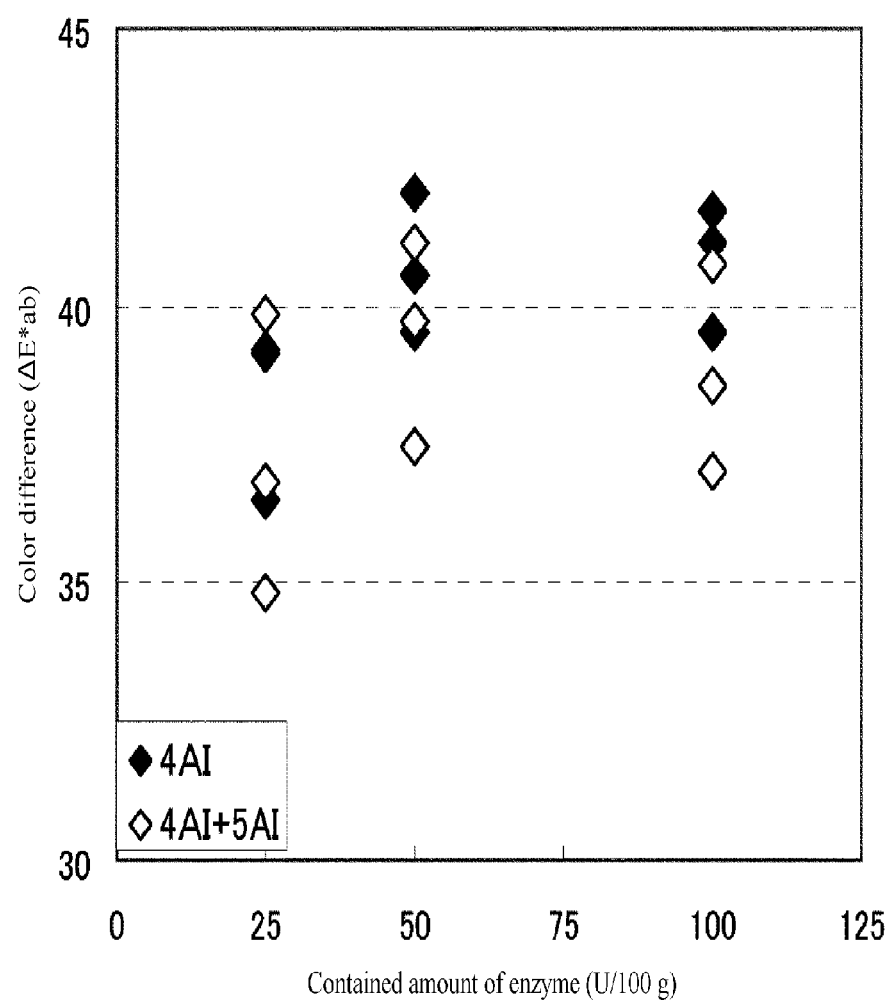
FIG. 14 shows the result of the dyeing tests using indole compounds as chromogenic substrates. The relationship between the concentration of the enzyme and the dyeing effect was examined. The values in the cases when dyed under a condition of pH 7 were compared for BO and PMO, and the values in the cases when dyed under a condition of pH 9 were compared for $H_2O_2$. 4AI: 4-aminoindole, 5AI: 5-aminoindole.
Figure 15:
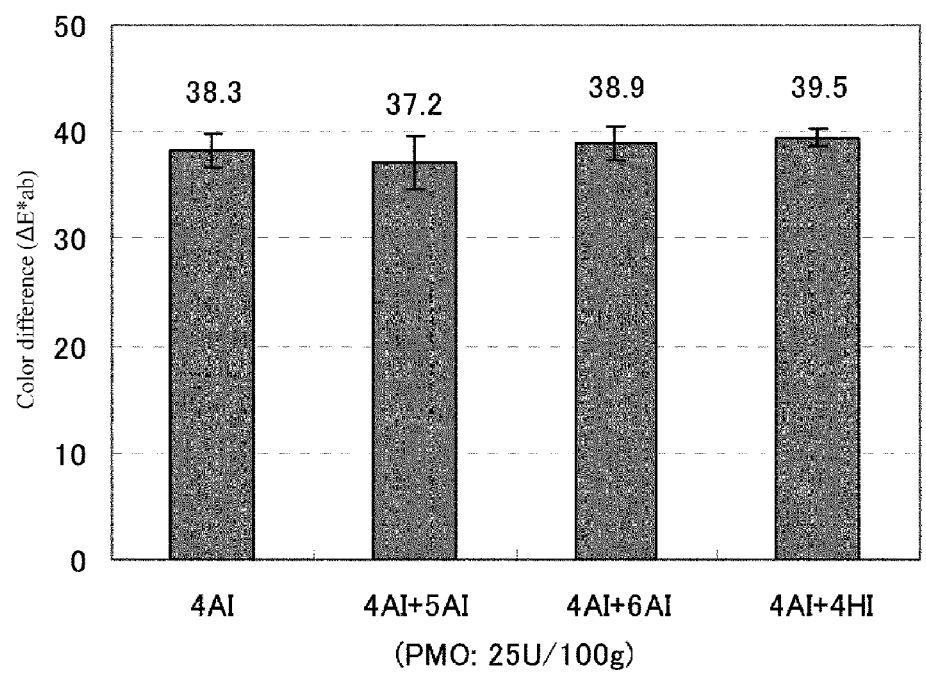
FIG. 15 shows the result of the dyeing tests using indole compounds as chromogenic substrates. The relationship between the combination of the indole compounds and the dyeing effect was examined. The values in the cases when dyed under a condition of pH 7 were compared for BO and PMO, and the values in the cases when dyed under a condition of pH 9 were compared for $H_2O_2$. 4AI: 4-aminoindole, 5AI: 5-aminoindole, 6AI: 6-aminoindole, 4HI: 4-hydroxyindole.
Figure 16:
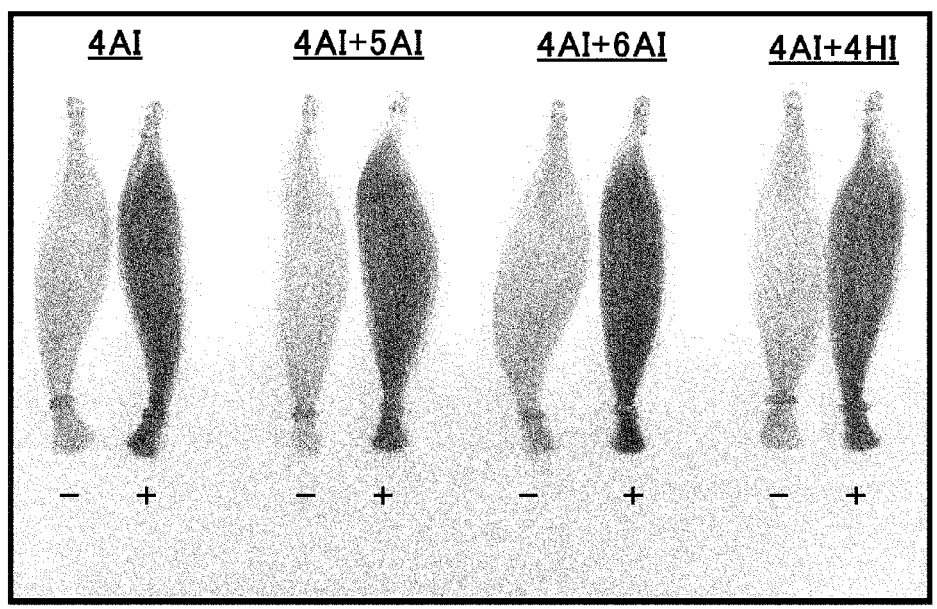
FIG. 16 shows the result of the dyeing tests using indole compounds as chromogenic substrates (pH 7.0). Different indole compounds were used by various combinations, and the changes in the color were examined. 4AI: 4-aminoindole, 5AI: 5-aminoindole, 6AI: 6-aminoindole, 4HI: 4-hydroxyindole. –: without enzyme, + with enzyme (25 U/100 g of PMO was added).

The test results are shown in Tables 15 and 16 and FIGS. 14 to 16. In either condition, the peak of the color difference was at an enzyme concentration of around 50 U/100 g (FIG. 14). When various indole compounds were used in combination, a significant difference in the color difference was not be able to be confirmed (FIG. 15), but a change in the color was observed (Table 16, FIG. 16).

TABLE 15

| | Substrate 1 | Substrate 2 | Oxidizing agent | Concentration | pH | ΔE * ab | | | ΔE * ab Aver. | Standard deviation |
|---|---|---|---|---|---|---|---|---|---|---|
| Control | 4AI: 1% | — | — | — | 7 | 1.0 | 1.7 | 1.2 | 1.3 | 0.33 |
| Control | 4AI: 0.5% | 5AI: 0.5% | — | — | 7 | 4.6 | 2.3 | 3.5 | 3.5 | 1.16 |

TABLE 15-continued

| | Substrate 1 | Substrate 2 | Oxidizing agent | Concentration | pH | ΔE * ab | | | ΔE * ab Aver. | Standard deviation |
|---|---|---|---|---|---|---|---|---|---|---|
| Control | 4AI: 0.5% | 6AI: 0.5% | — | — | 7 | 3.2 | 5.8 | 4.5 | 4.5 | 1.29 |
| Control | 4AI: 0.5% | 4HI: 0.5% | — | — | 7 | 2.5 | 0.7 | 1.7 | 1.6 | 0.90 |
| Condition 1 | 4AI: 1% | — | PMO | 25U/100 g | 7 | 39.2 | 36.5 | 39.2 | 38.3 | 1.56 |
| Condition 2 | 4AI: 1% | — | PMO | 50U/100 g | 7 | 42.1 | 40.6 | 39.5 | 40.7 | 1.27 |
| Condition 3 | 4AI: 1% | — | PMO | 100U/100 g | 7 | 41.1 | 39.5 | 41.7 | 40.8 | 1.15 |
| Condition 4 | 4AI: 1% | — | $H_2O_2$ | 3% | 9 | 18.7 | 19.6 | 18.9 | 19.1 | 0.46 |
| Condition 5 | 4AI: 0.5% | 5AI: 0.5% | PMO | 25U/100 g | 7 | 36.8 | 39.8 | 34.8 | 37.2 | 2.51 |
| Condition 6 | 4AI: 0.5% | 5AI: 0.5% | PMO | 50U/100 g | 7 | 41.1 | 37.5 | 39.8 | 39.5 | 1.83 |
| Condition 7 | 4AI: 0.5% | 5AI: 0.5% | PMO | 100U/100 g | 7 | 37.0 | 38.6 | 40.7 | 38.8 | 1.86 |
| Condition 8 | 4AI: 0.5% | 5AI: 0.5% | $H_2O_2$ | 3% | 9 | 23.9 | 24.4 | 22.0 | 23.4 | 1.26 |
| Condition 9 | 4AI: 0.5% | 6AI: 0.5% | PMO | 25U/100 g | 7 | 37.9 | 40.8 | 38.0 | 38.9 | 1.61 |
| Condition 10 | 4AI: 0.5% | 4HI: 0.5% | PMO | 25U/100 g | 7 | 38.6 | 40.3 | 39.5 | 39.5 | 0.86 |

4AI: 4-aminoindole
5AI: 5-aminoindole
6AI: 6-aminoindole
4HI: 4-hydroxyindole

TABLE 16

| Substrate | L * (D65) | a * (D65) | b * (D65) |
|---|---|---|---|
| 4AI | 36.9 ± 1.7 | −2.2 ± 0.1 | 1.2 ± 0.4 |
| 4AI + 5AI | 36.7 ± 2.3 | 0.9 ± 0.4 | 3.3 ± 1.0 |
| 4AI + 6AI | 34.8 ± 1.7 | −0.5 ± 0.3 | 3.3 ± 0.4 |
| 4AI + 4AI | 35.9 ± 0.8 | −1.1 ± 0.1 | 0.3 ± 0.4 |

Figure 17:
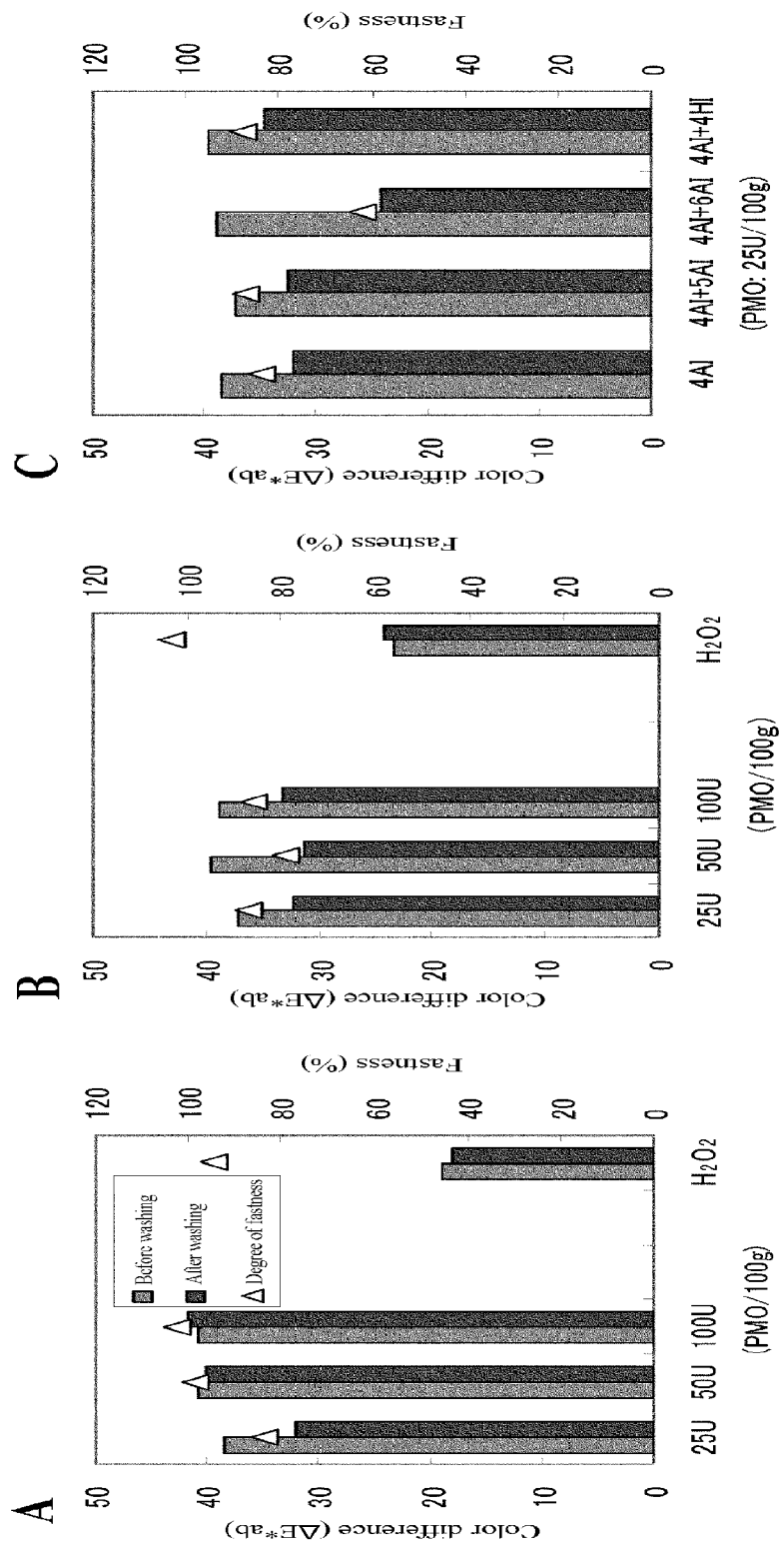
FIG. 17 shows the results of the shampoo resistance tests. Different indole compounds were used by various combinations, and the shampoo resistances were compared. A: the result in the case when 5-aminoindole was used as a chromogenic substrate, B: the result in the case when 4-aminoindole and 5-aminoindole were used in combination as chromogenic substrates, and C: the comparison between the various combinations (25 U/100 g of PMO was added). 4AI: 4-aminoindole, 5AI: 5-aminoindole, 6AI: 6-aminoindole, 4HI: 4-hydroxyindole.

4AI: 4-aminoindole
5AI: 5-aminoindole
6AI: 6-aminoindole
4HI: 4-hydroxyindole (2) Results of Shampoo Resistance Tests The test results are shown in Table 17 and FIG. 17. In the case when 5AI was used, a tendency that the degree of fastness increased (color loss is low) when the enzyme concentration was increased was shown (FIG. 17A).

TABLE 17

| | Substrate 1 | Substrate 2 | Oxidizing agent | Concentration | pH | ΔE Aver. (before washing) | ΔE Aver. (after washing) | Fastness (%) |
|---|---|---|---|---|---|---|---|---|
| Condition 1 | 4AI: 1% | — | PMO | 0.25U/g | 7 | 38.3 | 32.0 | 83.7 |
| Condition 2 | 4AI: 1% | — | PMO | 0.5U/g | 7 | 40.7 | 40.0 | 98.2 |
| Condition 3 | 4AI: 1% | — | PMO | 1U/g | 7 | 40.8 | 41.7 | 102.2 |
| Condition 4 | 4AI: 1% | — | $H_2O_2$ | 3% | 9 | 19.1 | 18.0 | 94.3 |
| Condition 5 | 4AI: 0.5% | 5AI: 0.5% | PMO | 0.25U/g | 7 | 37.2 | 32.4 | 87.1 |
| Condition 6 | 4AI: 0.5% | 5AI: 0.5% | PMO | 0.5U/g | 7 | 39.5 | 31.2 | 79.1 |
| Condition 7 | 4AI: 0.5% | 5AI: 0.5% | PMO | 1U/g | 7 | 38.8 | 33.2 | 85.7 |
| Condition 8 | 4AI: 0.5% | 5AI: 0.5% | $H_2O_2$ | 3% | 9 | 23.4 | 24.2 | 103.3 |
| Condition 9 | 4AI: 0.5% | 6AI: 0.5% | PMO | 0.25U/g | 7 | 38.9 | 24.2 | 62.2 |
| Condition 10 | 4AI: 0.5% | 4HI: 0.5% | PMO | 0.25U/g | 7 | 39.5 | 34.6 | 87.7 |

4AI: 4-aminoindole
5AI: 5-aminoindole
6AI: 6-aminoindole
4HI: 4-hydroxyindole

As mentioned above, it was possible to conduct more effective hair dyeing when the modified enzyme was used than that of the case when hydrogen peroxide was used, even in the case when an indole compound (4-aminoindole, 5-aminoindole or the like), which is considered to be highly safe, was adopted as a chromogenic substrate. Furthermore, it was possible to dye in various color tones depending on the kinds and combinations of the indole compounds used.

F. Dyeing Effects in Cases when Indole Analogues are Used as Chromogenic Substrates 3

The dyeing effect in the case when an indole compound 5,6-dihydroxyindole was used as a chromogenic substrate was examined. 5,6-Dihydroxyindole is a melanin precursor and polymerizes in the presence of oxygen to form a melanin pigment. Although 5,6-dihydroxyindole is highly safe, the difficulty in handling and low dyeing effect thereof are considered to be problems.

1. Process

The test method and evaluation were conducted according to D. (Dyeing effects in cases when the indole analogues were used as chromogenic substrates 1), except that 0.3% by weight of 5,6-dihydroxyindole was used as a chromogenic substrate.

2. Results (1) Confirmation of Dyeing Effects by Hair Dye Tests

Figure 18:
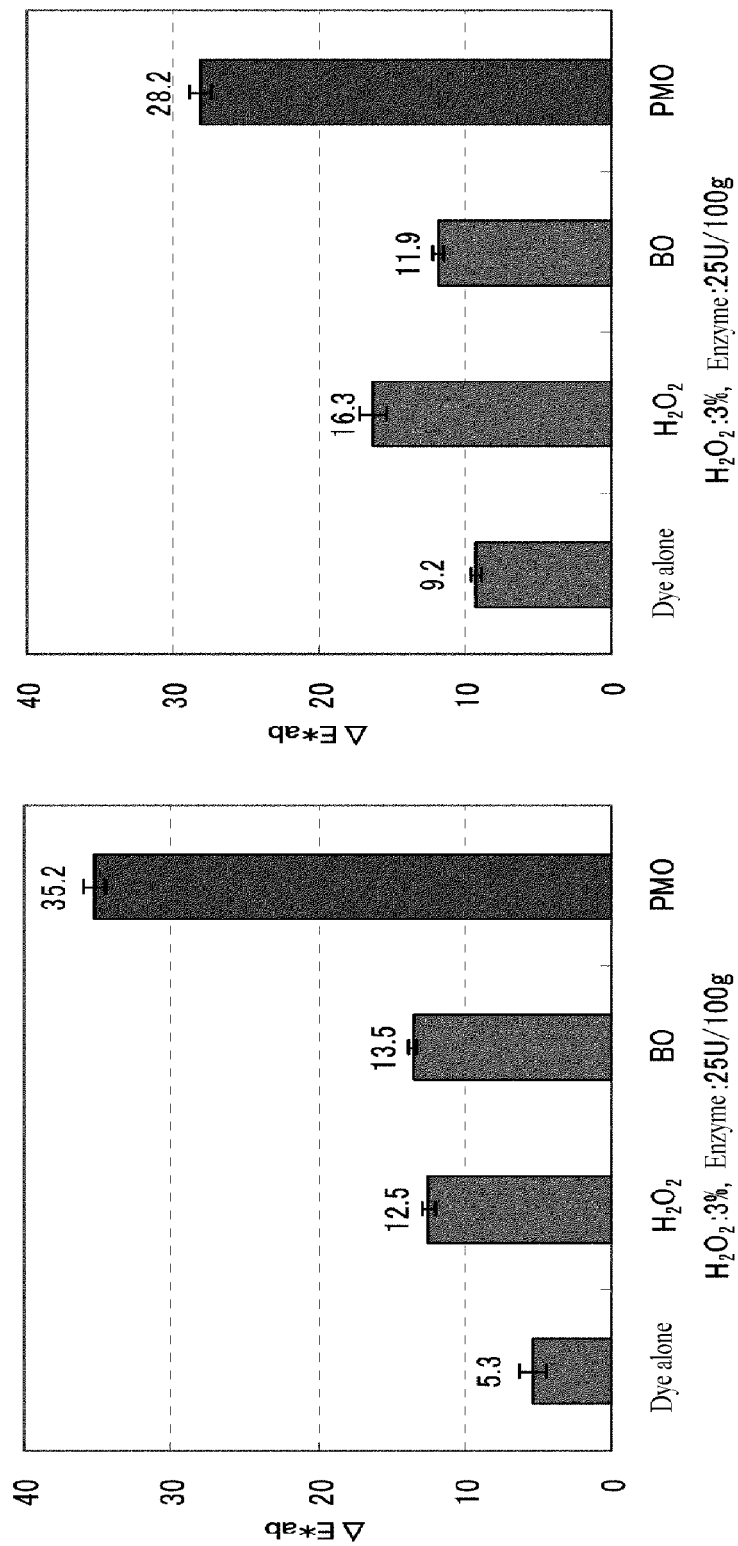
FIG. 18 shows the result of the dyeing tests using an indole compound 5,6-dihydroxyindole as a chromogenic substrate. For the cases when dyeing was conducted under a condition of pH 7.0 (left) and the cases when dyeing was conducted under a condition of pH 9.0 (right), the results of the dyeing (color differences $\Delta E^*ab$) were compared among hydrogen peroxide ($H_2O_2$), BO (unmodified enzyme) and PMO (modified enzyme).
Figure 19:
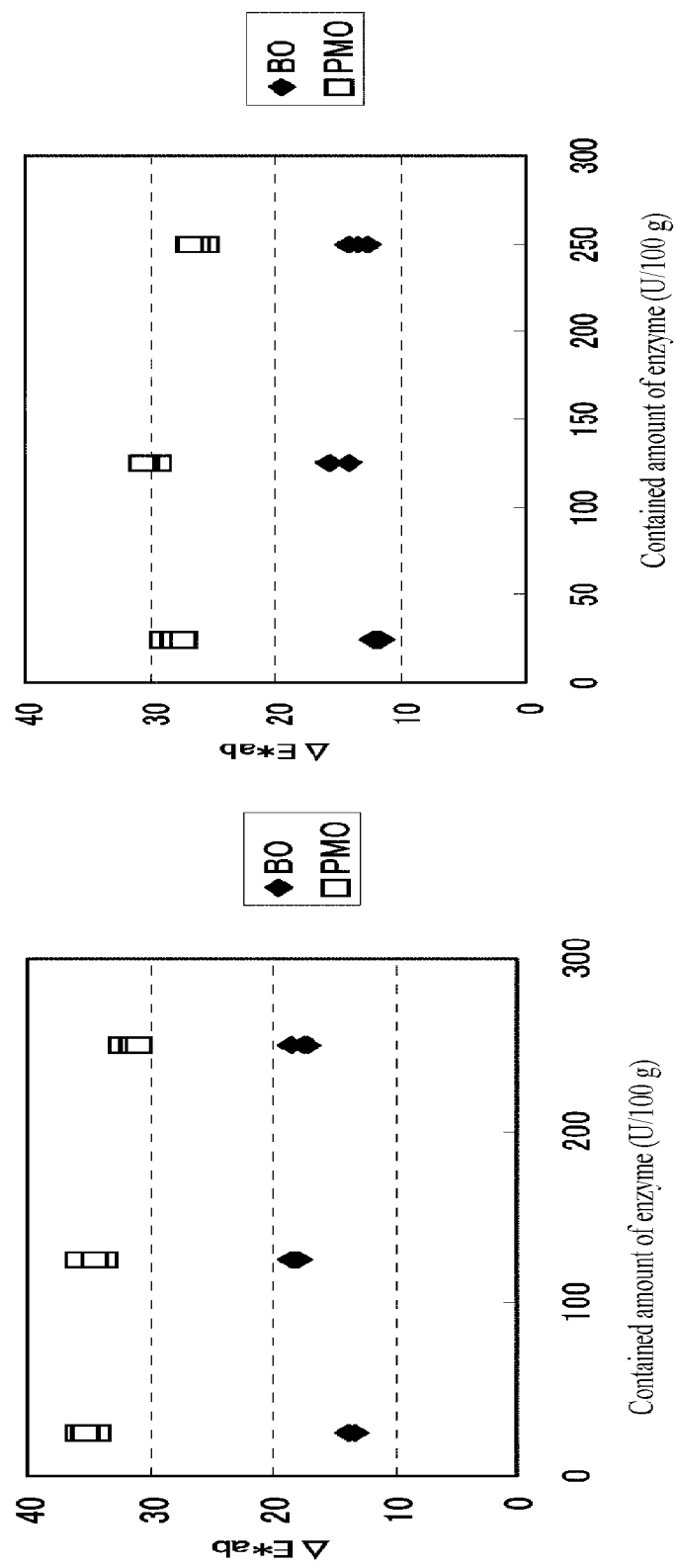
FIG. 19 shows the result of the dyeing tests using an indole compound 5,6-dihydroxyindole as a chromogenic substrate. For the cases when dyeing was conducted under a condition of pH 7.0 (left) and the cases when dyeing was conducted under a condition of pH 9.0 (right), the relationships between the amount of the enzyme and the dyeing effect (color difference $\Delta E^*ab$) were compared between BO (unmodified enzyme) and PMO (modified enzyme).
Figure 20:
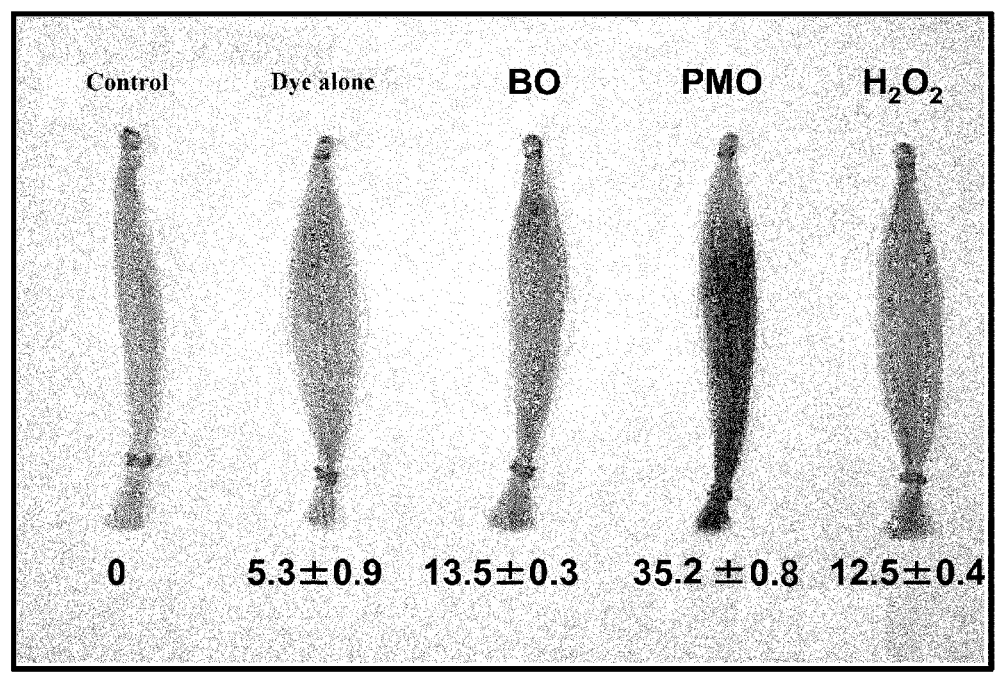
FIG. 20 shows the result of the dyeing tests using an indole compound 5,6-dihydroxyindole as a chromogenic substrate. The hairs were dyed at pH 7.0 by using various oxidizing agents (BO: unmodified enzyme, PMO: modified enzyme, $H_2O_2$: hydrogen peroxide) and compared. The control is the hair before the treatment. BO and PMO were each added by 25 U/100 g. Furthermore, $H_2O_2$ was added by 3% (final concentration). The values show color differences from white hairs ($\Delta E^*ab$).

The test results are shown in Table 18 and FIGS. 18 to 20.

TABLE 18

| Oxidizing agent | pH | Concentration | ΔE * ab | | | ΔE * ab (Aver.) | Standard deviation |
|---|---|---|---|---|---|---|---|
| None | 7 | — | 4.7 | 6.4 | 4.9 | 5.3 | 0.9 |
| BO | 7 | 25U/100 g | 13.4 | 13.8 | 13.3 | 13.5 | 0.3 |

TABLE 18-continued

| Oxidizing agent | pH | Concentration | ΔE * ab | | | ΔE * ab (Aver.) | Standard deviation |
|---|---|---|---|---|---|---|---|
| BO | 7 | 125U/100 g | 18.4 | 17.9 | 18.2 | 18.1 | 0.2 |
| BO | 7 | 250U/100 g | 17.2 | 18.4 | 17.4 | 17.7 | 0.7 |
| PMO | 7 | 25U/100 g | 34.4 | 35.9 | 35.3 | 35.2 | 0.8 |
| PMO | 7 | 125U/100 g | 33.8 | 35.8 | 34.6 | 34.7 | 1.0 |
| PMO | 7 | 250U/100 g | 32.1 | 31.5 | 30.9 | 31.5 | 0.6 |
| $H_2O_2$ | 7 | 3% | 12.8 | 12.6 | 12.0 | 12.5 | 0.4 |
| None | 9 | — | 9.0 | 9.0 | 9.7 | 9.2 | 0.4 |
| BO | 9 | 25U/100 g | 11.5 | 12.1 | 11.9 | 11.9 | 0.3 |
| BO | 9 | 125U/100 g | 14.1 | 15.6 | 14.1 | 14.6 | 0.9 |
| BO | 9 | 250U/100 g | 14.1 | 13.4 | 12.6 | 13.4 | 0.8 |
| PMO | 9 | 25U/100 g | 28.8 | 28.2 | 27.5 | 28.2 | 0.7 |
| PMO | 9 | 125U/100 g | 29.5 | 30.5 | 30.5 | 30.2 | 0.6 |
| PMO | 9 | 250U/100 g | 25.5 | 26.3 | 26.7 | 26.2 | 0.6 |
| $H_2O_2$ | 9 | 3% | 15.8 | 15.7 | 17.3 | 16.3 | 0.9 |

It is understood that an excellent dyeing effect can be obtained by using PMO as an oxidizing agent. PMO has a dramatically higher oxidizing effect than that of hydrogen peroxide (FIG. 18). On the other hand, unlike the case when hydrogen peroxide is used, in the case when PMO is used, the dyeing effect is higher under the condition of pH 7.0 than that under the condition of pH 9.0 (FIGS. 18 and 19). From this result, it can be said that a high dyeing effect can be obtained while suppressing the damage of hairs by using PMO. This feature is a great advantage in practical use. With respect to the relationship between the enzyme amount and dyeing effect, the highest dyeing effect was shown at the lowest use amount (25 U/100 g). This result supports that PMO shows a high oxidizing effect (dyeing effect).

As mentioned above, it was shown that PMO is also effective in the case when 5,6-dihydroxyindole is used as a chromogenic substrate, in other words, effective dyeing is possible by using PMO.

INDUSTRIAL APPLICABILITY

The dyeing agent of the present invention is utilized for dyeing using oxidation dyes. The dyeing agent of the present invention can be applied to various dyeing processes. Specifically, the present invention is effective for hair dyeing.

This invention is not limited at all by the above-mentioned embodiments for carrying out the invention and the explanations in Examples. Various embodiments of modification are also encompassed in this invention within the scope that does not deviate from the descriptions in the claims and can be easily conceived by persons skilled in the art. The whole contents of the articles, patent publications and patents, and the like which are clearly indicated in the present description are incorporated herein by reference.

The invention claimed is:

1. A dyeing agent comprising a modified enzyme obtained by adding positive charge by a chemical modification with an amine to an enzyme selected from the group consisting of an enzyme specified as EC 1.10.3.1, an enzyme specified as EC 1.10.3.2, an enzyme specified as EC 1.3.3.5, an enzyme specified as EC 1.10.3.4, an enzyme specified as EC 1.10.3.3 and an enzyme specified as EC 1.14.18.1.

2. The dyeing agent according to claim 1, which is formed by combining with an oxidation dye.

3. The dyeing agent according to claim 2, which is a one-component type comprising the oxidation dye and the modified enzyme.

4. The dyeing agent according to claim 2, which is a two-component type consisting of a first element comprising the oxidation dye and a second element comprising the modified enzyme.

5. The dyeing agent according to claim 1, which is for use in dyeing keratin fibers.

6. The dyeing agent according to claim 5, wherein the keratin fibers are human hairs.

7. The dyeing agent according to claim 2, wherein the oxidation dye is one or more compound(s) selected from the group consisting of phenylenediamine, aminophenol, cresol, toluenediamine, naphthol, indole, indoline and derivatives thereof.

8. The dyeing agent according to claim 2, wherein the oxidation dye is one or more compound(s) selected from the group consisting of paraphenylenediamine, paraminophenol, paratoluenediamine, 4-aminoindole, 5-aminoindole, 6-aminoindole, 4-hydroxyindole and 5,6-dihydroxyindole.

9. The dyeing agent according to claim 1, wherein the enzyme is bilirubin oxidase.

10. A process for dyeing, comprising a step of treating fibers or processed fibers with the dyeing agent according to claim 1.

11. The process for dyeing according to claim 10, wherein the fibers are keratin fibers.

12. The process for dyeing according to claim 11, wherein the keratin fibers are human hairs.

13. The process for dyeing according to claim 12, wherein the treatment is conducted under a condition of a pH of 7.0 to 8.0.

* * * * *

```
                         SEQUENCE LISTING

<160> NUMBER OF SEQ ID NOS: 1

<210> SEQ ID NO 1
<211> LENGTH: 572
<212> TYPE: PRT
<213> ORGANISM: Myrothecium verrucaria

<400> SEQUENCE: 1

Met Phe Lys His Thr Leu Gly Ala Ala Ala Leu Ser Leu Leu Phe Asn
1               5                   10                  15

Ser Asn Ala Val Gln Ala Ser Pro Val Pro Glu Thr Ser Pro Ala Thr
            20                  25                  30

Gly His Leu Phe Lys Arg Val Ala Gln Ile Ser Pro Gln Tyr Pro Met
        35                  40                  45

Phe Thr Val Pro Leu Pro Ile Pro Pro Val Lys Gln Pro Arg Leu Thr
    50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
    130                 135                 140

Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
                165                 170                 175

His Ile Thr Ala Glu Asn Ala Tyr Arg Gly Gln Ala Gly Leu Tyr Met
            180                 185                 190
```

-continued

```
Leu Thr Asp Pro Ala Glu Asp Ala Leu Asn Leu Pro Ser Gly Tyr Gly
        195                 200                 205
Glu Phe Asp Ile Pro Met Ile Leu Thr Ser Lys Gln Tyr Thr Ala Asn
        210                 215                 220
Gly Asn Leu Val Thr Thr Asn Gly Glu Leu Asn Ser Phe Trp Gly Asp
225                 230                 235                 240
Val Ile His Val Asn Gly Gln Pro Trp Pro Phe Lys Asn Val Glu Pro
                245                 250                 255
Arg Lys Tyr Arg Phe Arg Phe Leu Asp Ala Ala Val Ser Arg Ser Phe
                260                 265                 270
Gly Leu Tyr Phe Ala Asp Thr Asp Ala Ile Asp Thr Arg Leu Pro Phe
                275                 280                 285
Lys Val Ile Ala Ser Asp Ser Gly Leu Leu His Pro Ala Asp Thr
        290                 295                 300
Ser Leu Leu Tyr Ile Ser Met Ala Glu Arg Tyr Glu Val Val Phe Asp
305                 310                 315                 320
Phe Ser Asp Tyr Ala Gly Lys Thr Ile Glu Leu Arg Asn Leu Gly Gly
                325                 330                 335
Ser Ile Gly Gly Ile Gly Thr Asp Thr Asp Tyr Asp Asn Thr Asp Lys
                340                 345                 350
Val Met Arg Phe Val Val Ala Asp Asp Thr Thr Gln Pro Asp Thr Ser
        355                 360                 365
Val Val Pro Ala Asn Leu Arg Asp Val Pro Phe Pro Ser Pro Thr Thr
370                 375                 380
Asn Thr Pro Arg Gln Phe Arg Phe Gly Arg Thr Gly Pro Thr Trp Thr
385                 390                 395                 400
Ile Asn Gly Val Ala Phe Ala Asp Val Gln Asn Arg Leu Leu Ala Asn
                405                 410                 415
Val Pro Val Gly Thr Val Glu Arg Trp Glu Leu Ile Asn Ala Gly Asn
                420                 425                 430
Gly Trp Thr His Pro Ile His Ile His Leu Val Asp Phe Lys Val Ile
        435                 440                 445
Ser Arg Thr Ser Gly Asn Asn Ala Arg Thr Val Met Pro Tyr Glu Ser
        450                 455                 460
Gly Leu Lys Asp Val Val Trp Leu Gly Arg Arg Glu Thr Val Val Val
465                 470                 475                 480
Glu Ala His Tyr Ala Pro Phe Pro Gly Val Tyr Met Phe His Cys His
                485                 490                 495
Asn Leu Ile His Glu Asp His Asp Met Met Ala Ala Phe Asn Ala Thr
                500                 505                 510
Val Leu Pro Asp Tyr Gly Tyr Asn Ala Thr Val Phe Val Asp Pro Met
        515                 520                 525
Glu Glu Leu Trp Gln Ala Arg Pro Tyr Glu Leu Gly Glu Phe Gln Ala
        530                 535                 540
Gln Ser Gly Gln Phe Ser Val Gln Ala Val Thr Glu Arg Ile Gln Thr
545                 550                 555                 560
Met Ala Glu Tyr Arg Pro Tyr Ala Ala Asp Glu
                565                 570
```